US008557980B2

(12) United States Patent
Burke et al.

(10) Patent No.: US 8,557,980 B2
(45) Date of Patent: Oct. 15, 2013

(54) METHODS FOR FORMING PROTECTED ORGANOBORONIC ACIDS

(75) Inventors: Martin D. Burke, Champaign, IL (US); Graham R. Dick, Vancouver (CA); David M. Knapp, Boonville, IN (US); Eric P. Gillis, Wallingford, CT (US); Jenna A. Klubnick, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 302 days.

(21) Appl. No.: 13/030,833

(22) Filed: Feb. 18, 2011

(65) Prior Publication Data

US 2011/0201806 A1    Aug. 18, 2011

Related U.S. Application Data

(60) Provisional application No. 61/305,603, filed on Feb. 18, 2010.

(51) Int. Cl.
  *C07F 5/02*    (2006.01)
(52) U.S. Cl.
  USPC ........................................................ 540/467
(58) Field of Classification Search
  None
  See application file for complete search history.

(56) References Cited

U.S. PATENT DOCUMENTS

| | | | |
|---|---|---|---|
| 6,096,906 A | 8/2000 | Piscopio et al. | |
| 8,338,601 B2 * | 12/2012 | Burke et al. | 546/13 |
| 2003/0114666 A1 | 6/2003 | Ellsworth et al. | |
| 2005/0038287 A1 | 2/2005 | Scherer et al. | |
| 2007/0027327 A1 | 2/2007 | Wu et al. | |
| 2009/0030238 A1 | 1/2009 | Burke et al. | |
| 2010/0121062 A1 | 5/2010 | Burke et al. | |

FOREIGN PATENT DOCUMENTS

| | | |
|---|---|---|
| EP | 1375496 A1 | 1/2004 |
| WO | WO-2007/016355 A2 | 2/2007 |

OTHER PUBLICATIONS

U.S. Appl. No. 11/937,338, filed Nov. 8, 2007, Burke et al.
U.S. Appl. No. 12/567,443, filed Sep. 25, 2009, Burke et al.
U.S. Appl. No. 13/190,223, filed Jul. 25, 2011, Burke et al.
Arnone, A., et al., "Studies on ratanhiae radix. II Isolation of ratanhine, a new dineolignan from the medicinal ratanhiae radix", *Gazz. Chim. Ital.*, 120:397-401 (Italy, 1990).
Barder, T. E., et al., "Catalysts for Suzuki-Miyaura coupling processes: Scope and studies of the effect of ligand structure", *J. Am. Chem. Soc.*, 127:4685-4696 (2005).
Billingsley, K., et al., "Highly efficient monophoshine-based catalyst for the palladium-catalyzed Suzuki-Miyaura reaction of heteroaryl halides a", *J. Am. Chem. Soc.*, 129:3358-3366 (2007).
Billingsley, K.L., et al., "A general and efficient method for the Suzuki-Miyaura coupling of 2-pyridyl nucleophiles", *Angew. Chem. Int. Ed.*, 47:4695-4698 (2008).
Bouillon, A., et al., "Synthesis of novel halopyridinylboronic acids and esters. Part 4: Halopyridin-2-yl-boronic acids and esters are stable,", *Tetrahedron*, 59(50):10043-10049 (Dec. 8, 2003).
Brown, H. C., et al., "Chiral synthesis via organoboranes. XVI. Boroxazolidones derived from alpha-amino acids and borinic or boronic esters.", *Journal of Organometallic Chemistry*, 341(1-3):73-81 (The Netherlands, 1988).
Caruthers, M. H. , "Gene synthesis machines: DNA chemistry and its uses", *Science*, 230(4723):281-285 (1985).
Contreras, R., et al., "The N-B coordination in hindered cyclic thexylboronic esters derived from diethanolamines", *J. Organomet. Chem.*, 1983, 246:213-217 (1983).
Deng, X., et al., "An efficient convergent synthesis of novel anisotropic adsorbates based on nanometer-sized and tripod-shaped oligophenyl", *J. Org. Chem.*, 67:5279-5283 (2002).
Garrigues, B., et al., "Mono- and bicyclic derivatives of tetracoordinated boron and alpha- amino diacids: reactions with various nucleophiles", *Journal of Organometallic Chemistry*, 314(1-2):19-24 (The Netherlands, 1986). (Abstract).
Garrigues, B., et al., "Synthesis of mono- and bicyclic boron derivatives tetracoordinated with alpha-amino diacids", *Journal of Organometallic Chemistry*, 302(2):153-158 (The Netherlands, 1986). (Abstract).
Gillis, E., et al., "A Simple and Modular Strategy for Small Molecule Synthesis: Iterative Suzuki-Miyaura Coupling of B-Protected Haloboronic Acid Building Blocks", *J. Amer. Chem. Soc.*, 129(21):6716-6717 (United States, May 9, 2007).
Gravel, M., et al., "Universal solid-phase approach for the immobilization, derivatization, and resin-to-resin transfer reactions of boronic", *J. Org. Chem.*, 67:3-15 (2002).
Gros, P., et al., "New polystyrene-supported stable source of 2-pyridylboron reagent for Suzuki couplings in combinatorial chemistry", *Tetrahedron Lett.*, 45:6239-6241 (2004).
Hall, D. G., "Boronic Acids", *Boronic Acids*, 3-14, (Wiley-VCH , Germany, 2005).
Hodgson, P. B., et al., "The preparation of a stable 2-pyridylboronate and its reactivity in the Suzuki-Miyaura cross-coupling reaction", *Tetrahedron Letters*, 45(4):685-687 (Jan. 19, 2004).
Hohn, E., et al., "Enantiomerically pure cydopropane building blocks: synthesis and transformation of 2-iodocyclopropylboronic esters", *Adv. Synth. Catal.*, 346:863-866 (2004).
Holmes, D., et al., "One-Pot Borylation/Animation Reactions: Syntheses of Arylamine Boronate Esters from Halogenated Arenes", *Org. Lett.*, 8(7):1407-1410 (2006).

(Continued)

*Primary Examiner* — Noble Jarrell
(74) *Attorney, Agent, or Firm* — Dana M. Gordon; Foley Hoag LLP

(57) ABSTRACT

Described are methods of forming protected boronic acids that provide in a manner that is straightforward, scalable, and cost-effective a wide variety of building blocks, such as building blocks containing complex and/or pharmaceutically important structures, and/or provide simple or complex protected organoboronic acid building blocks. A first method includes reacting an imino-di-carboxylic acid and an organoboronate salt. A second method includes reacting a N-substituted morpholine dione and an organoboronic acid.

18 Claims, 10 Drawing Sheets

(56) References Cited

OTHER PUBLICATIONS

Jones, N.A., et al., "Synthesis of 2,2'-Bipyridyl-Type Compounds via the Suzuki-Miyaura Cross-Coupling Reaction", *J. Heterocyclic Chem.*, 2007, 44:363-367 (2007).

Kirchhoff, J. H., et al., "Boronic Acids: New Coupling Partners in Room-Temperature Suzuki Reactions of Alkyl Bromides.", *J. Am. Chem. Soc.*, 124:13662-13663 (2002).

Kitamura, Y., et al.; "Heterogeneous Pd/C-catalyzed ligand-free Suzuki-Miyaura coupling reaction using argyl boronic esters," *Tetrahedron*, 63(43):10596-10602 (Oct. 22, 2007).

Littke, A. F., et al., "Versatile Catalysts for the Suzuki Cross-Coupling of Arylboronic Acids with Aryl and Vinyl Halides and Triflates under Mild Conditions", *J. Am. Chem. Soc.*, 122:4020-4028 (2000).

Mancilla, T., et al., "Molecular and crystalline structure of (N→B)-phenyl [N-methyliminodacetate-O,O',N] borane", *VI Congreso Iberomaericano de Quimica Inorganica*, 290-293 (Mexico, Apr. 20, 1997). (Abstract).

Mancilla, T., et al., "Alpha and N-alkylation of bicyclic organylboronic esters derived from iminodiacetic acid", *Main Group Metal Chemistry*, 15(1):9-17 (1992).

Mancilla, T., et al., "Crystal and molecular structure of (N→B) phenyl [N-methyliminodiacetate-O,O',N] borane", *Main Group Metal Chemistry*, 20(1):31-36 (1997).

Mancilla, T., et al., "New bicyclic organylboronic esters derived from iminodiacetic acids", *Journal of Organometallic Chemistry*, 307(1):1-6 (The Netherlands, 1986).

Mancilla, T., et al., "Syntheses and characterization of (N→B) phenyl [N-arylaminodiacetate-O,O',N] boranes and N-arylaminodiacetic acids", *Heteroatom Chemistry*, 5(5/6):455-462 (1994).

Mancilla, T., et al., "Syntheses of (N→B) phenyl [*N*-alkylaminodiacetate-O,O',*N*] boranes", *Polyhedron*, 15(21):3777-3785 (Great Britain, 1996).

Mancilla, T., et al., "Synthesis and characterization of (N→B) phenyl [*N*-alkyl-*N*-(2-alkyl) aminodiacetate-O,O',*N*] boranes and phenyl[*N*-alkyl-(2-alkyl)aminodiacetate-O,O',N]boranes", *Polyhedron*, 26(5):1023-1028 (Mar. 6, 2007).

Mancilla, T., et al., "Synthesis and characterization of new (N→B) phenyl substituted [N-benzyliminodiacetate-O,O',N] boranes", *Arkivoc*, 6:366-376 (2005).

Matos, et al., "Alkylboranes in the Suzuki-Miyaura Coupling: Stereochemical and Mechanistic Studies", *J. Org. Chem.*, 63:461-470 (1998).

Matteson, D. S., "Introduction to Borane Chemistry", In: Stereodirected Synthesis with Organoboranes, 1-20 (Springer, Germany, 1995).

Merrifield, R. B., "Solid Phase Synthesis", *Angew. Chem., Int. Ed.*, 24(10):799-810 (1985).

Miyaura, et al., "Palladium-Catalyzed Cross-Coupling Reactions of Organoboron Compounds", *Chem. Rev.*, 95:2457-2483 (1995).

Miyaura, N., "Cross-coupling reaction of organoboron compounds via base-assisted transmetalation to palladium(II) complexes", *J. Organomet. Chem.*, 653:54-57 (2002).

Molander G. A., et al., "Palladium-Catalyzed Suzuki-Miyaura Cross-Coupling Reactions of Potassium Aryl- and Heteroaryltrifluoroborates", 68:4302-4314 (2003).

Molander G. A., et al., "Scope of the Suzuki-Miyaura Cross-Coupling Reactions of Potassium Heteroaryltrifluoroborates", *J. Org. Chem.*, 74:973-980 (2009).

Nicolaou K.C., et al., "Palladium-Catalyzed Cross-Coupling Reactions in Total Synthesis", *Angew. Chem., Int. Ed.*, 44:4442-4489 (2005).

Noguchi H., et al., "Boron-Masking Strategy for the Selective Synthesis of Oligoarenes via Iterative Suzuki-Miyaura Coupling", *J. Am. Chem. Soc.*, 129:758-759 (2007).

Pagano N., et al., "Ruthenium half-sandwich complexes as protein kinase inhibitors: derivatization of the pyridocarbazole pharmacophore ligand", *Org. Biomol. Chem.*, 5:1218-1227 (2007).

Plante O. J., et al., "Automated Solid-Phase Synthesis of Oligosaccharides", *Science*, 291:1523-1527 (2001).

Stewart, S.K., et al.; "Synthesis of *trans*-arylvinylboronates via a palladium catalysed cross-coupling of a vinylboronate ester with aryl halides," *J. Organometallic Chemistry*, 482(1-2):293-300 (Nov. 29, 1994).

Tyrell E., et al., "The Synthesis and Applications of Heterocyclic Boronic Acids", *Synthesis*, 4:469-483 (2004).

Vedejs E., et al., "Internal Coordination at Tin Promotes Selective Alkyl Transfer in the Stille Coupling Reaction", *J. Am. Chem. Soc.*, 114:6556-6558 (1992).

Young J. K., et al., "Synthesis of Sequence Specific Phenylacetylene Oligomers on an Insoluble Solid Support", *J. Am. Chem. Soc.*, 116:10841-10842 (1994).

Zhang J., et al.,"Nanoarchitectures. 1. Controlled Synthesis of Phenylacetylene Sequences", *J. Am. Chem. Soc.*, 114:2273-2274 (1992).

International Search Report and Written Opinion of the International Searching Authority from related application PCT/US2011/025446 dated Nov. 28, 2011.

* cited by examiner

| entry | conditions | bath temp (°C) | % yield |
|---|---|---|---|
| 1 | addition of 3 as a solution in THF | 50 | 4 |
| 2 | addition of 3 as a solution in THF | 110 | 46 |
| 3 | addition of 3 as a solution in THF | 150 | 58 |

METHODS FOR FORMING PROTECTED ORGANOBORONIC ACIDS

RELATED APPLICATIONS

This application claims the benefit of priority to U.S. Provisional Patent Application Ser. No. 61/305,603, filed Feb. 18, 2010.

GOVERNMENT SUPPORT

The subject matter of this application was made with government support from the National Science Foundation under grant number Career 0747778. The U.S. Government has certain rights in this invention.

BACKGROUND

The Suzuki-Miyaura reaction is a palladium- or nickel-catalyzed cross coupling between a boronic acid or a boronic ester, and an organohalide or an organo-pseudohalide. (Miyaura, N.; Suzuki, A. *Chem. Rev.* 1995, 95, 2457-2483) This cross coupling transformation is a powerful method for C—C bond formation in complex molecule synthesis. The reaction is tolerant of functional groups, and has become increasingly general and widespread in its use for coupling of organic compounds. (Barder, T. E.; Walker, S. D.; Martinelli, J. R.; Buchwald, S. L. *J. Am. Chem. Soc.* 2005, 127, 4685-4696; Billingsley, K.; Buchwald, S. L. *J. Am. Chem. Soc.* 2007, 129, 3358-3366; Littke, A. F.; Dai, C.; Fu, G. C. *J. Am. Chem. Soc.* 2000, 122, 4020-4028.; Nicolaou, K. C., et al. *Angew. Chem. Int. Ed.* 2005, 44, 4442) A difficult aspect of the Suzuki-Miyaura reaction is the sensitivity of the boronic acid functional group to many common reagent, which makes the synthesis of structurally complex organoboronic acid building blocks challenging. (Hall, D. G. *Boronic Acids*, Wiley-VCH, Germany, 2005, 3-14; Tyrell, 2003)

One area of research on the Suzuki-Miyaura reaction is the development of protecting groups for the boronic acid functional group. In one example of a boronic acid protecting group, each of the two B—OH groups is converted into a boronic ester group (>B—O—R) or a boronic amide group (>B—NH—R), where R is an organic group. (Deng, X.; Mayeux, A.; Cai, C. *J. Org. Chem.* 2002, 67, 5279-5283; Hohn, E.; Pietruszka, J. *Adv. Synth. Catal.* 2004, 346, 863-866; Holmes, D., et al. *Org. Lett.* 2006, 8, 1407-1410; Noguchi, H.; Hojo, K.; Suginome, M. *J. Am. Chem. Soc.* 2007, 129, 758-759) The heteroatom-boron bonds in these protected compounds tend to be very strong, however, and the relatively harsh conditions required for cleaving these ligands to provide the free boronic acid group typically are incompatible with complex molecule synthesis. In another example, three organoboronic acid molecules can be condensed to form a cyclic boroxine protecting group. (Kerins, F.; O'Shea, D. F. *J. Org. Chem.* 2002, 67, 4968-4971) These protected organoboronic acids, however, tend to be unstable to long term storage. The reactivity of a boronic acid group also may be decreased by conversion of the boronic acid group into a tetracoordinate anion, such as $[R-BF_3]^-$, where R represents an organic group, as a salt with a counterion such as $K^+$ or $Na^+$. (Molander, G. A; Ellis, N. *Acc. Chem. Res.* 2007, 40, 275-286) Another class of tetracoordinate boron anions, $[R-B(OH)_3]^-$, has been reported in the context of purifying organoboronic acids for use in the Suzuki-Miyaura reaction. (Cammidge, A. N. et al. *Organic Letters* 2006, 8, 4071-4074) In each of these systems, the boron itself is not protected from the Suzuki-Miyaura reaction, but can be used directly in the coupling transformation.

The most useful and versatile system for protecting boronic acids is the use of an imino-di-carboxylic acid boronate protecting group. Imino-di-carboxylic acid boronates, such as N-methyliminodiacetic acid (MIDA), can be used to protect boronic acid functional groups from a variety of chemical reactions. (U.S. Pat. App. Pub. 2009/0030238; Gillis, E. P.; Burke, M. D. *J. Am. Chem. Soc.* 2007, 129, 6716-6717; Lee, S. J., Gray, K. C., Paek, J. S., Burke, M. D. *J. Am. Chem. Soc.* 2008, 130, 466-468) The MIDA boronates are stable to air and to purification by chromatography, and do not cross-couple under anhydrous conditions. However, the protecting group can be hydrolyzed with aqueous base to release the corresponding unprotected organoboronic acid. Thus, MIDA boronates can be used as convenient surrogates for organoboronic acids under aqueous base-promoted Suzuki-Miyaura coupling conditions, and the deprotection and cross-coupling may be performed as a single step in the presence of aqueous base. This approach has been shown to be effective for a wide variety of organoboronic acids.

The base used to simultaneously deprotect the MIDA boronate and promote the cross-coupling reaction may be a mild base. Deprotection of MIDA boronates with a mild base can provide a slower release of the unprotected organoboronic acid into the reaction mixture than that provided through deprotection with a strong base. This slower release can allow cross-coupling to occur between an organohalide or an organo-pseudohalide and an organoboronic acid that would otherwise degrade during the reaction. This slower release also can allow cross-coupling to occur with organoboronic acids that cannot be prepared or isolated in pure form. The method of deprotecting and cross-coupling with a mild base is described, for example, in copending U.S. patent application Ser. No. 12/567,443, entitled "Slow Release of Organoboronic Acids In Cross-Coupling Reactions", with inventors Martin D. Burke et al., which is incorporated herein by reference.

A challenge that remains in the MIDA protecting system is the formation of protected organoboronic acid building blocks for use in synthesis of complex organic compounds. It would be desirable to provide a wide variety of building blocks, and particularly to provide building blocks containing complex and/or pharmaceutically important structures. It also would be desirable to provide a method of forming simple or complex protected organoboronic acid building blocks that is more straightforward, scalable, and cost-effective.

Regarding the formation of building blocks containing complex and/or pharmaceutically important structures, one such class of structures is the 2-heterocyclic groups. Many pharmaceuticals contain 2-heterocyclic subunits, with 2-pyridyl, 2-furan, 2-thiophene, 2-indole, 2-oxazole, and 2-thiazole being among the most common. These same substructures are also prevalent in natural products, particularly those derived from NRPS and hybrid PKS/NRPS biosynthesis pathways. 2-Substituted heterocycles also commonly appear in probe reagents for chemical biological studies, metal-complexing ligands, and a variety of materials for molecular electronic, display, energy capture, energy storage, and field effect transistor devices.

Although they are among the most desirable synthetic building blocks with respect to low cost, minimal environmental impact, and lack of toxicity, 2-heterocyclic boronic acids are notoriously unstable, which often precludes their effective utilization. Many different types of surrogates have been developed, including trifluoroborate salts, trialkoxy or trihydroxyborate salts, diethanolamine adducts, sterically bulky boronic esters and boroxines. Advances in the development of 2-heterocyclic silanolates have also recently been reported. However, it remains a challenge to develop air-stable, chemically pure, and highly effective surrogates for some of the most challenging classes of 2-heterocyclic building blocks, e.g., the notoriously unstable 2-pyridyl derivatives. 2-heterocyclic stannanes represent stable and effective alternatives, but these reagents suffer from substantial toxicity.

A variety of 2-heterocyclic MIDA boronates have been used successfully in cross-coupling reactions. (U.S. patent application Ser. No. 12/567,443) The 2-heterocyclic MIDA boronate building blocks were not formed by reaction of MIDA with the corresponding unprotected boronic acids, however, as the unprotected boronic acids are notoriously unstable. While alternative methods have been used to form MIDA boronates of boronic acids that would be unstable if unprotected, these methods have met with mixed success. In particular, formation of 2-heterocyclic MIDA boronates containing nitrogen at the 2-position in the heterocyclic group have been cumbersome and low yielding, and have not shown characteristics of scalability. For example, the formation of 2-pyridyl MIDA boronate by reaction of lithium 2-pyridyl-triisopropylboronate with MIDA in DMSO at 75° C. provided only a 27% yield. Thus, it would be desirable to provide an improved method for forming MIDA boronates containing complex and/or pharmaceutically important structures.

Regarding the formation of simple or complex protected organoboronic acid building blocks in a manner that is more straightforward, scalable, and cost-effective, many MIDA boronates can be prepared by refluxing a mixture of the corresponding boronic acid and MIDA in toluene and DMSO in a Dean-Stark apparatus. The DMSO conventionally has been required to partially dissolve the highly polar MIDA reagent. Refluxing in a Dean-Stark apparatus conventionally has been necessary to remove the water that is generated during the complexation process. This conventional method presents a number of challenges, however. Some boronic acids can undergo thermal decomposition at the elevated temperatures of refluxing DMSO, resulting in decreased yields of the MIDA boronate. Moreover, the MIDA reagent can cause the reaction conditions to be acidic, which can be detrimental to acid-sensitive boronic acids. Finally, the DMSO used in the reaction can be challenging to completely remove from the MIDA boronate product.

For example, in the preparation of 5-bromopentanyl MIDA boronate from 5-bromopentanyl boronic acid using the conventional Dean-Stark conditions (PhMe:DMSO 10:1), the 5-bromopentanyl boronic acid substantially decomposed, resulting in low yields of 5-bromopentanyl MIDA boronate. Moreover, the reaction product included residual DMSO, which was difficult to remove.

The number of commercially available boronic acids currently is over 3,000. Moreover, methods for making many other boronic acids are well-known. Thus, it would be desirable to provide a simple and efficient process to transform directly any boronic acid into the corresponding MIDA boronate.

SUMMARY

In one aspect, the invention provides a method of forming a protected boronic acid, which includes reacting in a reaction mixture an imino-di-carboxylic acid and an organoboronate salt represented by formula (I):

where $R^1$ represents an organic group; $R^2$, $R^3$ and $R^4$ independently are an alkyl group or an aryl group; and $M^+$ is a metal ion, a metal halide ion or an ammonium ion. The reaction mixture further includes a polar aprotic solvent, and the reacting includes maintaining the reaction mixture at a temperature of at least 100° C. The method further includes forming a protected organoboronic acid represented by formula (III) in the reaction mixture:

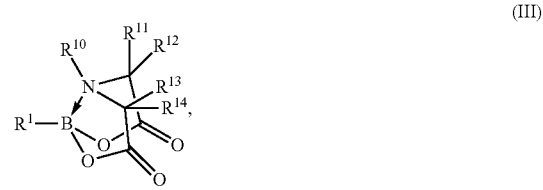

where $R^{10}$, $R^{11}$, $R^{12}$, $R^{13}$ and $R^{14}$ independently are a hydrogen group or an organic group.

In another aspect, the invention provides a method of forming a protected boronic acid, which includes reacting in a reaction mixture a N-substituted morpholine dione and an organoboronic acid represented by formula (XII):

where $R^1$ represents an organic group. The reaction mixture further includes a polar aprotic solvent. The method further includes forming a protected organoboronic acid represented by formula (III) in the reaction mixture:

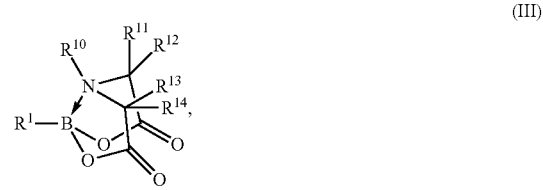

where $R^{10}$ represents an organic group; and $R^{11}$, $R^{12}$, $R^{13}$ and $R^{14}$ independently are a hydrogen group or an organic group.

The following definitions are included to provide a clear and consistent understanding of the specification and claims.

The term "organoboronic acid" means a compound represented by formula (XII):

where $R^1$ is an organic group that is bonded to the boron through a boron-carbon bond.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "organic group" means a group containing at least one carbon atom.

The term "protected organoboronic acid" means a chemical transform of an organoboronic acid, in which the boron has a lower chemical reactivity relative to the original organoboronic acid.

The term "chemical transform" of a substance means a product of a chemical transformation of the substance, where the product has a chemical structure different from that of the substance. A chemical transform of a substance may or may not actually be formed from the substance.

The term "chemical transformation" means the conversion of a substance into a product, irrespective of reagents or mechanisms involved.

The term "sp$^3$ hybridization" means that an atom is bonded and/or coordinated in a configuration having a tetrahedral character of at least 50%. For tetracoordinate boron atoms, the tetrahedral character of the boron atom is calculated by the method of Hopfl, H., *J. Organomet. Chem.* 1999, 581, 129-149. In this method, the tetrahedral character is defined as:

$$THC_{DA}[\%]=100\times[1-(\Sigma_{n=1-6}|109.5-\theta_n|°/90°)]$$

where $\theta_n$ is one of the six bond angles of the boron atom.

The term "protecting group" means an organic group bonded to at least one atom, where the atom has a lower chemical activity than when it is not bonded to the protecting group. For boron containing compounds, the term excludes non-organic groups used to lower the chemical activity of the boron, such as the F$^-$ and OH$^-$ ligands of —BF$_3^-$ and —B(OH)$_3^-$.

The term "conformationally rigid protecting group" means an organic protecting group that, when bonded to a boron atom, is determined to be conformationally rigid by the "conformational rigidity test".

The term "alkyl group" means a group formed by removing a hydrogen from a carbon of an alkane, where an alkane is an acyclic or cyclic compound consisting entirely of hydrogen atoms and saturated carbon atoms. An alkyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "heteroalkenyl group" means a group formed by removing a hydrogen from a carbon of a heteroalkene, where a heteroalkene is an acyclic or cyclic compound consisting entirely of hydrogen atoms, carbon atoms and one or more heteroatoms, and including at least one carbon-carbon double bond. A heteroalkenyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "heteroalkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "aryl group" means a group formed by removing a hydrogen from a ring carbon atom of an aromatic hydrocarbon. An aryl group may by monocyclic or polycyclic and may include one or more substituent groups.

The term "heteroaryl group" means a group formed by replacing one or more methine (—C═) and/or vinylene (—CH═CH—) groups in an aryl group with a trivalent or divalent heteroatom, respectively. A heteroaryl group may by monocyclic or polycyclic and may include one or more substituent groups.

The term "heterocyclic group" means a group formed by removing a hydrogen from a carbon of a heterocycle, where a heterocycle is a cyclic compound consisting entirely of hydrogen atoms, saturated carbon atoms, and one or more heteroatoms. A heterocyclic group may include one or more substituent groups. Heterocyclic groups include cyclic heteroalkyl groups, cyclic heteroalkenyl groups, cyclic heteroalkynyl groups and heteroaryl groups. A 2-heterocyclic groups is a heterocyclic group containing a heteroatom at the 2-position in the ring.

The term "substituent group" means a group that replaces one or more hydrogen atoms in a molecular entity.

The term "halogen group" means —F, —Cl, —Br or —I.

The term "organohalide" means an organic compound that includes at least one halogen group.

The term "haloorganoboronic acid" means an organoboronic acid in which the organic group bonded to the boron through a boron-carbon bond includes a halogen group or a pseudohalogen group.

The term "pseudohalogen group" means a group that has chemical reactivity similar to that of a halogen group. Examples of pseudohalogen groups include triflate (—O—S(═O)$_2$—CF$_3$), methanesulfonate (—O—S(═O)$_2$—CH$_3$), cyanate (—C≡N), azide (—N$_3$) thiocyanate (—N═C═S), thioether (—S—R), anhydride (—C(═O)—O—C(═O)—R), and phenyl selenide (—Se—C$_6$H$_5$).

The term "organo-pseudohalide" means an organic compound that includes at least one pseudohalogen group.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention.

DETAILED DESCRIPTION

Figure 1:
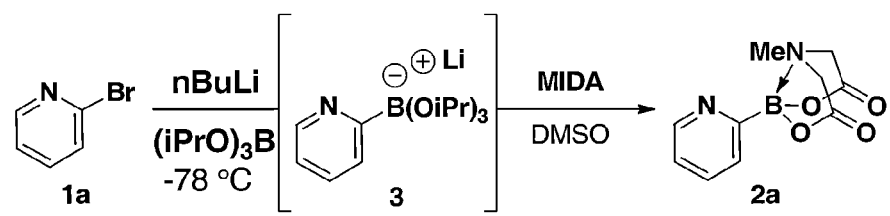
FIG. 1 represents chemical structures, reaction schemes and product yields for examples of the formation of a protected organoboronic acid from 2-bromo pyridine at various reaction temperatures.

In accordance with the present invention a first method of forming a protected boronic acid includes reacting in a reaction mixture an imino-di-carboxylic acid, and an organoboronate salt represented by formula (I):

$$[R^1\text{---}B(OR^2)(OR^3)(OR^4)]^-M^+ \qquad (I),$$

and forming a protected organoboronic acid represented by formula (III) in the reaction mixture:

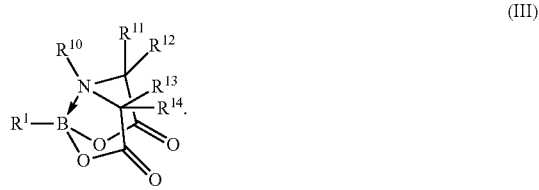

(III)

In formulas (I) and (III), $R^1$ is an organic group. In formula (I) $R^2$, $R^3$ and $R^4$ independently are an alkyl group or an aryl group, and $M^+$ is a metal ion, a metal halide ion or an ammonium ion. In formula (III), $R^{10}$, $R^{11}$, $R^{12}$, $R^{13}$ and $R^{14}$ independently are a hydrogen group or an organic group. The reaction mixture includes a polar aprotic solvent, and the reacting includes maintaining the reaction mixture at a temperature of at least 100° C.

An example of the method of forming a protected boronic acid by reaction of an organoboronate salt with an imino-di-carboxylic acid is represented in the following reaction scheme:

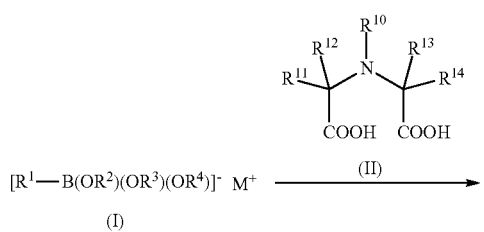

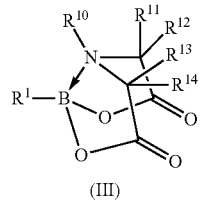

(III)

where the compound represented by formula (II) is the imino-di-carboxylic acid.

The $R^1$ group, in formulas (I) and (III), is bonded to the boron through a B—C bond. The $R^1$ group may be an alkyl group, a heteroalkyl group, an alkenyl group, a heteroalkenyl group, an alkynyl group, a heteroalkynyl group, an aryl group, a heteroaryl group, or a combination of at least two of these groups. Moreover, $R^1$ may include one or more substituent groups, which may include a heteroatom bonded to a carbon of the alkyl, heteroalkyl, alkenyl, heteroalkenyl, alkynyl, heteroalkynyl, aryl, and/or heteroaryl group.

The $R^1$ group may include one or more functional groups. Examples of functional groups that may be present as part of $R^1$ include halogen or pseudohalogen (—X), alcohol (—OH), aldehyde (—CH=O), ketone (>C(=O)), carboxylic acid (—C(=O)OH), thiol (—SH), sulfone, sulfoxide, amine, phosphine, phosphite, phosphate, and combinations of these. Moreover, examples of functional groups that may be present as part of $R^1$ include metal-containing groups, such as groups that contain metals such as tin (Sn), zinc (Zn), silicon (Si), boron, and combinations of these.

Examples of functional groups that may be present as part of $R^1$ include protected alcohols, such as alcohols protected as silyl ethers, for example trimethylsilyl ether (TMS), t-butyldiphenylsilyl ether (TBDPS), t-butyldimethylsilyl ether (TB-DMS), triisopropylsilyl ether (TIPS); alcohols protected as alkyl ethers, for example methoxymethyl ether (MOM), methoxyethoxymethyl ether (MEM), p-methoxybenzyl ether (PMB), tetrahydropyranyl ether (THP), methylthiomethyl ether; and alcohols protected as carbonyl groups, such as acetate or pivaloylate. Examples of functional groups that may be present as part of $R^1$ include protected carboxylic acids, such as carboxylic acids protected as esters, for example methyl ester, t-butyl ester, benzyl ester and silyl ester. Examples of functional groups that may be present as part of $R^1$ include protected amines, such as amines protected as carbamates, for example N-(trimethyl-silyl)-ethoxycarbamate (Teoc), 9-fluorenylmethyl carbamate (FMOC), benzylcarbamate (CBZ), t-butoxycarbamate (t-BOC); and amines protected as benzylamines.

In another example, the $R^1$-group may be represented by formula (IV):

$$Y\text{---}R^5\text{---}(R^6)_m\text{---} \qquad (IV),$$

where Y represents a halogen group or a pseudohalogen group; $R^5$ represents an aryl group or a heteroaryl group; $R^6$ represents an alkyl group, a heteroalkyl group, an alkenyl group, a heteroalkenyl group, an alkynyl group, a heteroalkynyl group, an aryl group, a heteroaryl group, or a combination of at least two of these groups; and m is 0 or 1. $R^5$ may be, for example, a heteroaryl group. Moreover, $R^5$ and $R^6$ independently may include one or more substituent groups, which may include a heteroatom bonded to a carbon of the $R^5$ or $R^6$ group. The $R^5$ and $R^6$ groups independently also may include one or more functional groups, as described for $R^1$ above. In one example, m is 1, and $R^6$ includes a 2-heterocyclic group.

For the protected organoboronic acid represented by formula (III), when $R^1$ is represented by formula (IV), the protected organoboronic acid is a protected haloorganoboronic acid or pseudohaloorganoboronic acid. The Y-group may undergo Suzuki-Miyaura cross-coupling with another compound that includes a free boronic acid group, without reaction of the boron of the protected organoboronic acid. Deprotection of the boron provides the free boronic acid group, which may then undergo Suzuki-Miyaura cross-coupling with another compound that includes a halogen group or a pseudohalogen group. These protected haloorganoboronic acids thus may be used as bifunctional building blocks for iterative synthesis through selective Suzuki-Miyaura transformations.

Preferably $R^1$ includes a heterocyclic group, an alkynyl group or an alkenyl group. Examples of heterocyclic groups include groups formed from a heterocyclic compound such as pyridine, indole, isoindole, indazole, purine, indolizidine, quinoline, isoquinoline, quinazoline, pteridine, quinolizidine, pyrrole, pyrazine, pyridazine, pyrimidine, imidazole, pyrasole, isoxazole, oxazole, thiazole, benzthiazole, furan, benzofuran, thiophene and benzothiophene.

Preferably $R^1$ is a 2-heterocyclic group, in which the group is bonded to the boron at the 2-position of the heterocyclic ring. Examples of 2-heterocyclic groups include 2-pyridyl, 2-indolyl, 2-isoindolyl, 2-indazolyl, 2-purinyl, 2-indolizidinyl, 2-quinolinyl, 2-isoquinolinyl, 2-quinazolinyl, 2-pteridinyl, 2-quinolizidinyl, 2-pyrrolyl, 2-pyrazinyl, 2-pyridazinyl, 2-pyrimidinyl, 2-imidazolyl, 2-pyrasolyl, 2-isoxazolyl, 2-oxazolyl, 2-thiazolyl, 2-benzthiazolyl, 2-furyl, 2-benzofuryl, 2-thiophenyl, and 2-benzthiophenyl. These groups independently also may include one or more substituent groups, which may include a heteroatom bonded to a carbon of the 2-heterocyclic group. Substituent groups, if present, may include one or more functional groups.

Preferably $R^1$ includes a 2-heterocyclic group containing nitrogen at the 1-position in the heterocyclic group. Examples of 2-heterocyclic groups containing nitrogen at the 1-position in the heterocyclic group include 2-pyridyl, 2-pyrazinyl, 2-thiazolyl, 2-pyrimidinyl, 2-(N-butoxycarbonyl-pyrollyl), and 2-(N-phenylsulfonate-indolyl).

The $R^2$, $R^3$ and $R^4$ groups independently are an alkyl group or an aryl group. Preferably $R^2$, $R^3$ and $R^4$ independently are an alkyl group or an aryl group having from 1 to 10 carbon atoms, and more preferably having from 1 to 6 carbon atoms. Preferably $R^2$, $R^3$ and $R^4$ independently are an alkyl group having from 1 to 4 carbon atoms, and more preferably having from 1 to 3 carbon atoms. Preferred groups for $R^2$, $R^3$ and $R^4$ include methyl (—$CH_3$) and isopropyl (—$CH(CH_3)_2$) groups. Preferably two or three of $R^2$, $R^3$ and $R^4$ are identical. Preferably $R^2$, $R^3$ and $R^4$ are identical and are methyl or isopropyl groups.

The $M^+$ ion is a counterion for the organoboronate anion. The $M^+$ ion is a metal ion, a metal halide ion or an ammonium ion. Preferably $M^+$ is an alkali metal ion, a transition metal ion, an alkaline earth metal halide ion, or a transition metal halide ion. Examples of $M^+$ include $Li^+$, $Na^+$, $K^+$, $MgX^+$, $CaX^+$, $Zn^+$, $Bu_4N^+$, where X is F, Cl, Br or I. Preferably $M^+$ is $Li^+$ or $MgX^+$.

The organoboronate salt represented by formula (I) may be formed by any of a variety of methods for forming boronate salts. In one example, an organohalide or an organopseudohalide is reacted with an organolithium reagent and then with a boronate ester, to form the organoboronate salt having $Li^+$ as the counterion to the organoboronate anion. This example may be represented by the following reaction scheme:

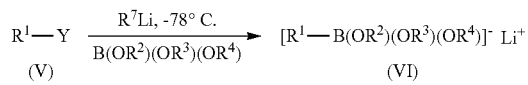

where $R^1$-$R^4$ are as described above, $R^7$ is a hydrocarbon group, and Y is a halogen or a pseudohalogen. The organohalide is represented by formula (V), and the organoboronate salt is represented by formula (VI).

In another example, an organic compound is reacted with a first organolithium reagent to form a second organolithium reagent in which a —H group from the organic compound has been replaced with a —Li group. This second organolithium reagent is then reacted with a boronate ester, to form the organoboronate salt having $Li^+$ as the counterion to the organoboronate anion. This example may be represented by the following reaction scheme:

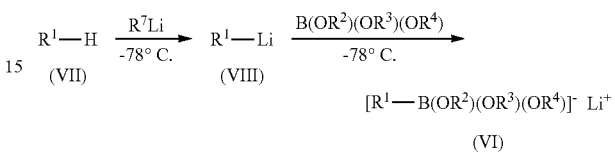

where $R^1$-$R^4$ are as described above, and $R^7$ is a hydrocarbon group. The organic compound is represented by formula (VII), the second organolithium reagent is represented by formula (VIII), and the organoboronate salt is represented by formula (VI). One potential advantage to this method of forming the organoboronate salt is that the pool of potential organic groups ($R^1$) may be larger, since the source of the organic group does not need to include a halogen or pseudohalogen group.

In another example, a Grignard reagent is reacted with a boronate ester, to form the organoboronate salt having $MgX^+$ as the counterion to the organoboronate anion. In a further example, the Grignard reagent optionally may be formed by reacting an organic compound with a mixed Mg/Li 2,2,6,6-tetramethylpiperidyl amide (Krasovskiy, A. *Angew. Chem. Int. Ed.* 2006, 45, 2958-2961). These examples may be represented by the following reaction scheme:

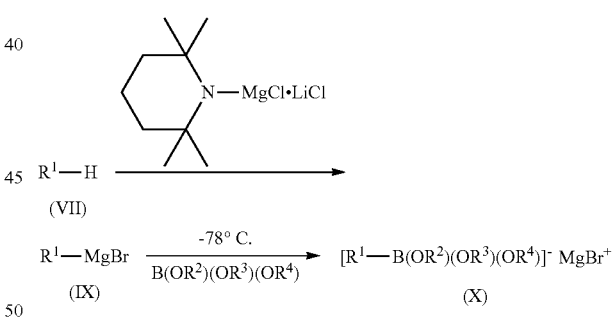

where $R^1$-$R^4$ are as described above. The Grignard reagent is represented by formula (IX), and the organoboronate salt is represented by formula (X). For the optional formation of the Grignard reagent, the organic compound represented by formula (VII) may be reacted with the mixed Mg/Li 2,2,6,6-tetramethylpiperidyl amide to provide the Grignard reagent represented by formula (IX).

The $R^{10}$, $R^{11}$, $R^{12}$, $R^{13}$ and $R^{14}$ groups, in formulas (II) and (III), independently are a hydrogen group or an organic group. $R^{10}$, $R^{11}$, $R^{12}$, $R^{13}$ and $R^{14}$ independently may be an alkyl group, a heteroalkyl group, an alkenyl group, a heteroalkenyl group, an alkynyl group, a heteroalkynyl group, an aryl group, a heteroaryl group, or a combination of at least two of these groups. If $R^{10}$ is an organic group, the imino-dicarboxylic acid of formula (II) is an N-substituted imino-dicarboxylic acid. In one example, $R^{10}$ is methyl, and each of $R^{11}$, $R^{12}$, $R^{13}$ and $R^{14}$ is hydrogen. In this example, the imino-di-carboxylic acid represented by formula (II) is N-methyliminodiacetic acid (MIDA).

The protected organoboronic acid represented by formula (III) includes boron having $sp^3$ hybridization, and the protecting group bonded to the boron is a conformationally rigid protecting group. Conformationally rigid protecting groups for boron are described, for example, in copending U.S. patent application Ser. No. 11/937,338, entitled "System For Controlling the Reactivity of Boronic Acids", with inventors Martin D. Burke et al., published as US 2009/0030238, which is incorporated herein by reference. Conformational rigidity of an organic protecting group bonded to a boron atom is determined by the following "conformational rigidity test". A 10 mg sample of a compound including a boron atom and an organic protecting group bonded to the boron is dissolved in dry $d_6$-DMSO and transferred to an NMR tube. The sample is then analyzed by $^1$H-NMR at temperatures ranging from 23° C. to 150° C. At each temperature, the sample shim is optimized, and a $^1$H-NMR spectrum obtained. If the protecting group is not conformationally rigid, then split peaks for a set of diastereotopic protons in the $^1$H-NMR spectrum obtained at 23° C. will coalesce into a single peak in the $^1$H-NMR spectrum obtained at 100° C. If the protecting group is conformationally rigid, then split peaks for a set of diastereotopic protons in the $^1$H-NMR spectrum obtained at 23° C. will remain split, and will not coalesce into a single peak in the $^1$H-NMR spectrum obtained at 90° C.

In one example the organoboronate salt represented by formula (I) is reacted with MIDA, producing a protected organoboronic acid represented by formula (III) in which $R^{20}$ is methyl, and each of $R^{21}$, $R^{22}$, $R^{23}$ and $R^{24}$ is hydrogen. The protected organoboronic acid of this example may be represented by formula (XI):

(XI)

The reaction mixture includes a polar aprotic solvent. Examples of polar aprotic solvents include tetrahydrofuran (THF), dioxane, dimethyl formamide (DMF), dimethyl sulfoxide (DMSO), toluene and xylene. Preferably the reaction mixture includes DMSO.

The reacting includes maintaining the reaction mixture at a temperature of at least 100° C. Preferably the reacting includes maintaining the reaction mixture at a temperature of at least 110° C., more preferably of at least 115° C. Preferably the reacting includes maintaining the reaction mixture at a temperature of from 100° C. to 200° C., more preferably from 100° C. to 175° C., more preferably from 110° C. to 150° C., and more preferably from 115° C. to 125° C.

Previously, it was believed that protected 2-heterocyclic organoboronic acids that included a MIDA boronate protecting group were susceptible to degradation when maintained in solution over 100° C. Surprisingly, it has now been discovered that 2-heterocyclic MIDA boronates can be stable at temperatures of a least 100° C., including temperatures of at least 110° C. and at least 115° C., and including temperatures of from 100° C. to 200° C., from 100° C. to 175° C., from 110° C. to 150° C., and from 115° C. to 125° C.

In certain embodiments of the aforementioned methods, $R^{10}$ is methyl, and each of $R^{11}$, $R^{12}$, $R^{13}$ and $R^{14}$ is hydrogen.

In certain embodiments of the aforementioned methods, the polar aprotic solvent is selected from the group consisting of tetrahydrofuran (THF), dioxane, dimethyl formamide (DMF), dimethyl sulfoxide (DMSO), toluene and xylene.

In certain embodiments of the aforementioned methods, the reaction mixture is at a temperature of from 100° C. to 200° C.

In certain embodiments of the aforementioned methods, $R^{10}$ is methyl, and each of $R^{11}$, $R^{12}$, $R^{13}$ and $R^{14}$ is hydrogen; and the polar aprotic solvent is selected from the group consisting of tetrahydrofuran (THF), dioxane, dimethyl formamide (DMF), dimethyl sulfoxide (DMSO), toluene and xylene.

In certain embodiments of the aforementioned methods, $R^{10}$ is methyl, and each of $R^{11}$, $R^{12}$, $R^{13}$ and $R^{14}$ is hydrogen; and the reaction mixture is at a temperature of from 100° C. to 200° C.

In certain embodiments of the aforementioned methods, $R^{10}$ is methyl, and each of $R^{11}$, $R^{12}$, $R^{13}$ and $R^{14}$ is hydrogen; the polar aprotic solvent is selected from the group consisting of tetrahydrofuran (THF), dioxane, dimethyl formamide (DMF), dimethyl sulfoxide (DMSO), toluene and xylene; and the reaction mixture is at a temperature of from 100° C. to 200° C.

In certain embodiments of the aforementioned methods, $R^{10}$ is methyl, and each of $R^{11}$, $R^{12}$, $R^{13}$ and $R^{14}$ is hydrogen; the polar aprotic solvent is selected from the group consisting of tetrahydrofuran (THF), dioxane, dimethyl formamide (DMF), dimethyl sulfoxide (DMSO), toluene and xylene; and the reaction mixture is at a temperature of from 100° C. to 175° C.

In certain embodiments of the aforementioned methods, $R^{10}$ is methyl, and each of $R^{11}$, $R^{12}$, $R^{13}$ and $R^{14}$ is hydrogen; and the polar aprotic solvent is dimethyl sulfoxide (DMSO).

In certain embodiments of the aforementioned methods, $R^{10}$ is methyl, and each of $R^{11}$, $R^{12}$, $R^{13}$ and $R^{14}$ is hydrogen; and the polar aprotic solvent is dimethyl sulfoxide (DMSO), toluene and xylene; and the reaction mixture is at a temperature of from 100° C. to 200° C.

In certain embodiments of the aforementioned methods, $R^{10}$ is methyl, and each of $R^{11}$, $R^{12}$, $R^{13}$ and $R^{14}$ is hydrogen; and the polar aprotic solvent is dimethyl sulfoxide (DMSO); and the reaction mixture is at a temperature of from 100° C. to 175° C.

In certain embodiments of the aforementioned methods, $R^{10}$ is methyl, and each of $R^{11}$, $R^{12}$, $R^{13}$ and $R^{14}$ is hydrogen; and the polar aprotic solvent is dimethyl sulfoxide (DMSO); and the reaction mixture is at a temperature of from 100° C. to 150° C.

In certain embodiments of the aforementioned methods, $R^{10}$ is methyl, and each of $R^{11}$, $R^{12}$, $R^{13}$ and $R^{14}$ is hydrogen; and the polar aprotic solvent is dimethyl sulfoxide (DMSO); and the reaction mixture is at a temperature of from 100° C. to 125° C.

FIG. 1 represents chemical structures, reaction schemes and product yields for examples of the formation of 2-pyridyl MIDA boronate 2a from 2-bromo pyridine 1a at various reaction temperatures. The lithium 2-pyridyl(triisopropyl)borate salt 3 can be formed by reaction of the 2-bromo pyridine 1a with n-butyl lithium (nBuLi) and triisopropyl boronate ester at −78° C. Although 3 is an effective reagent in other contexts, only a low yield of 4% of 2a was obtained when a freshly-prepared solution of 3 in THF was added to a stirred suspension of MIDA in DMSO at 50° C. The major byproducts observed in this reaction were pyridine and boric acid, which were consistent with competition between the formation of 2a and the protodeborylation of the notoriously labile 2-pyridyl-boron bond in 3. Attempts to avoid the undesirable protodeborylation by utilizing lower reaction temperatures did not improve the yield of 2a.

Surprisingly, increasing the reaction temperature from 50° C. to 110° C. provided a 10-fold increase in the yield of 2a. Also surprisingly, a further increase in the reaction temperature to 150° C. provided an increase in the yield to 58%. The unexpected stability of 2a at temperatures of at least 100° C. was confirmed by maintaining the protected organoboronic acid in solution in DMSO at 130° C. for one hour, while monitoring the solution by $^1$H NMR. One possible explanation for these surprising and unexpected results is that the undesired protodeborylation occurs prior to MIDA complexation. Thus, a higher reaction temperature enables a more rapid ligand exchange, which favors the formation of stable MIDA boronate 2a prior to the decomposition of its precursor 3.

Figure 2:
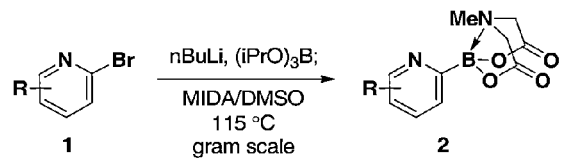
FIG. 2 represents chemical structures, reaction schemes and product yields for examples of the formation of protected organoboronic acids from various halogen-substituted heterocyclic compounds.

FIG. 2 represents chemical structures, reaction schemes and product yields for xamples of the formation of protected organoboronic acids 2a-2h from the various halogen-substituted heterocyclic compounds 1a-1h. The reaction of 2-bromo pyridine 1a with nBuLi and triisopropyl boronate ester at −78° C., followed by reaction of the resulting lithium 2-pyridyl(triisopropyl)borate salt with MIDA, was reproduced on a multigram scale to provide 2-pyridyl MIDA boronate 2a in 64% isolated yield (FIG. 2, entry 1). This protected organoboronic acid has been stored as a solid under an air atmosphere for more than 1 year without measurable decomposition.

Referring still to FIG. 2, a variety of halogen-substituted heterocyclic compounds 1b-1i may be reacted with nBuLi and triisopropyl boronate ester at −78° C., followed by a reaction of the resulting lithium 2-heterocyclic (triisopropyl) borate salts with MIDA, to form the corresponding 2-heterocyclic MIDA boronates 2b-2l. The 6-, 5-, and 4-methyl-2-pyridyl subunits appear in a wide variety of interesting and useful molecules, including pharmaceuticals, materials, and metal ligands, and the corresponding MIDA boronate building blocks 2b-d can be accessed readily using this method (FIG. 2, entries 2-4). The 6-methoxy-, and 6-, 5-, and 4-trifluoromethyl-2-pyridyl subunits represent a range of hydrogen bond donors and acceptors, as well as electron-withdrawing and electron-releasing groups, and the corresponding MIDA boronates 2e-2h were all prepared with this same procedure (FIG. 2, entries 5-8). Bromo-substituted 2-pyridyl MIDA boronate 2i and has the potential for a range of iterative cross-coupling applications, due to the presence of an aryl halide functionality in the protected organoboronic acid. Remarkably, each of the synthetic building blocks 2a-i is air- and chromatographically stable, highly crystalline, monomeric, and a free-flowing solid. Many aryl and heteroaryl bromides, including 2-bromopyridine, are commercially available and inexpensive. Thus, the method of forming a protected boronic acid by reaction of an organoboronate salt with an imino-di-carboxylic acid can provide straightforward access to a collection of air-stable 2-pyridyl building blocks, which is advantageous to research in drug discovery.

Figure 3:
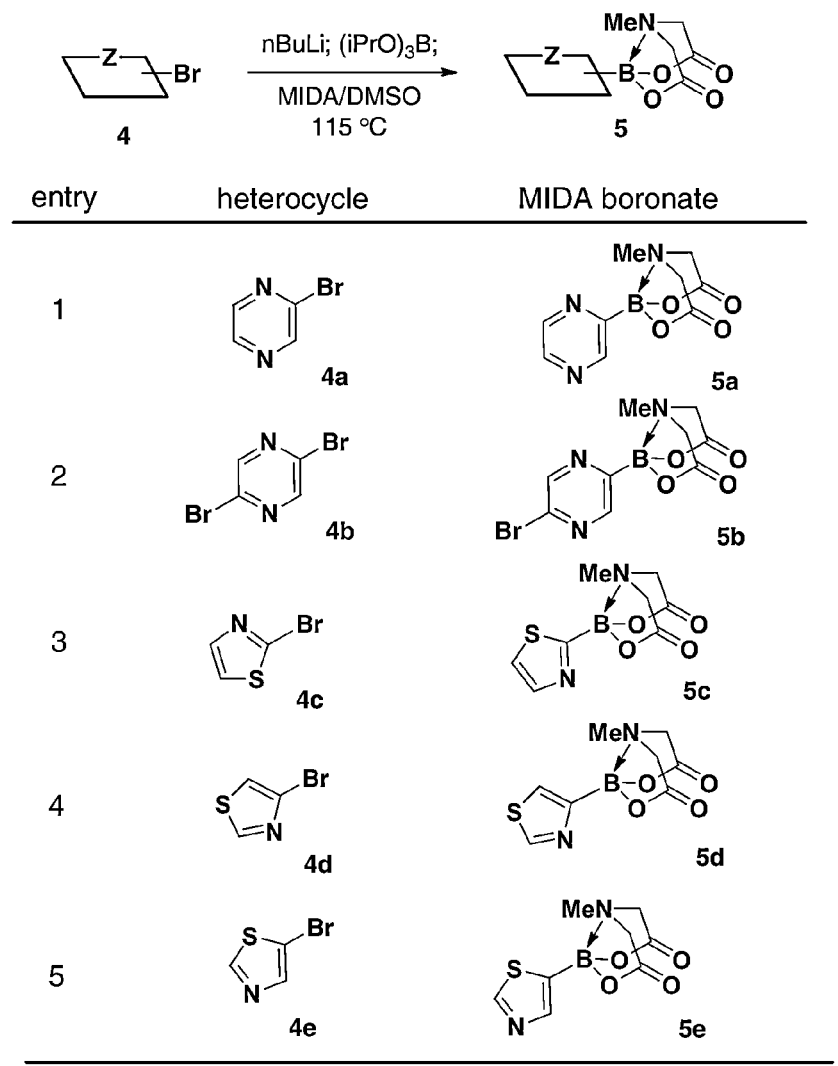
FIG. 3 represents chemical structures and reaction schemes for examples of the formation of protected organoboronic acids from various halogen-substituted heterocyclic compounds containing two ring heteroatoms.
Figure 4:
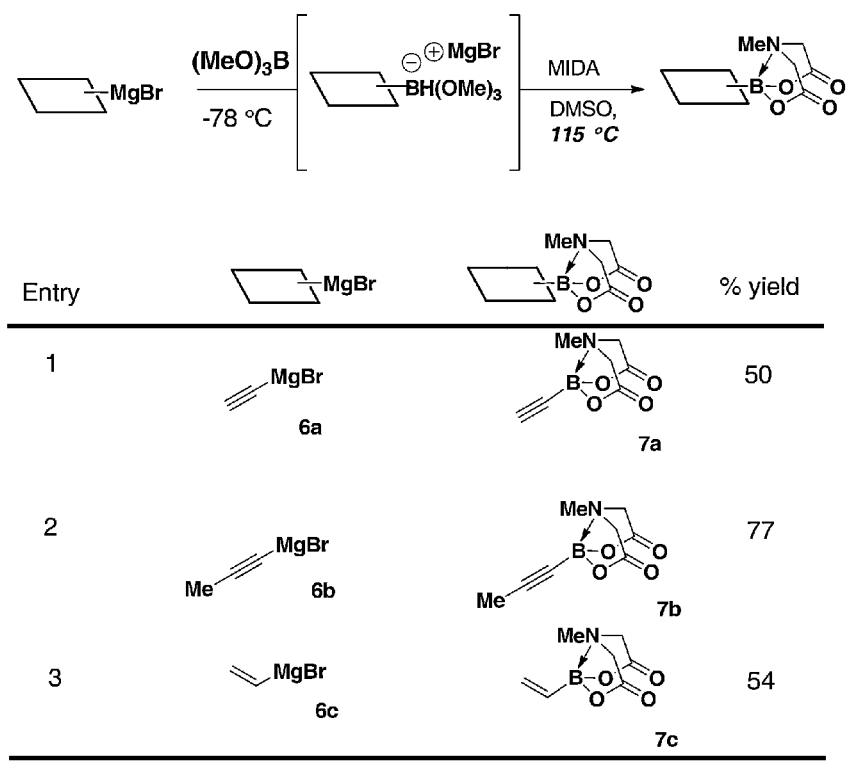
FIG. 4 represents chemical structures, reaction schemes and product yields for examples of the formation of protected organoboronic acids from various Grignard reagents.

FIG. 3 represents chemical structures and reaction schemes for examples of the formation of protected organoboronic acids 5a-5e from various halogen-substituted heterocyclic compounds containing two ring heteroatoms 4a-4e. The 2-pyrazine and thiazole subunits are important in medicinal chemistry, and the method of forming a protected boronic acid by reaction of an organoboronate salt with an imino-di-carboxylic acid successfully provided access to the 2-pyrazine MIDA boronates 5a-b (FIG. 4, entries 1 and 2) and to the thiazole MIDA boronates 5c-5e (FIG. 4, entries 3-5). The yield of 2-pyrazine MIDA boronate 5a was 43%. The yield of 5-thiazolyl MIDA boronate 5e was 44%.

FIG. 4 represents chemical structures, reaction schemes and product yields for examples of the formation of protected organoboronic acids 7a-7c from various Grignard reagents 6a-6c. The yields of protected organoboronic acids 7a-7c were 50%, 77% and 43%, respectively. Thus, an organoboronate salt having a MgBr$^+$ counterion instead of a Li$^+$ counterion can be reacted with MIDA in a polar aprotic solvent at a temperature of at least 100° C. to provide the corresponding protected organoboronic acid.

Figure 5:
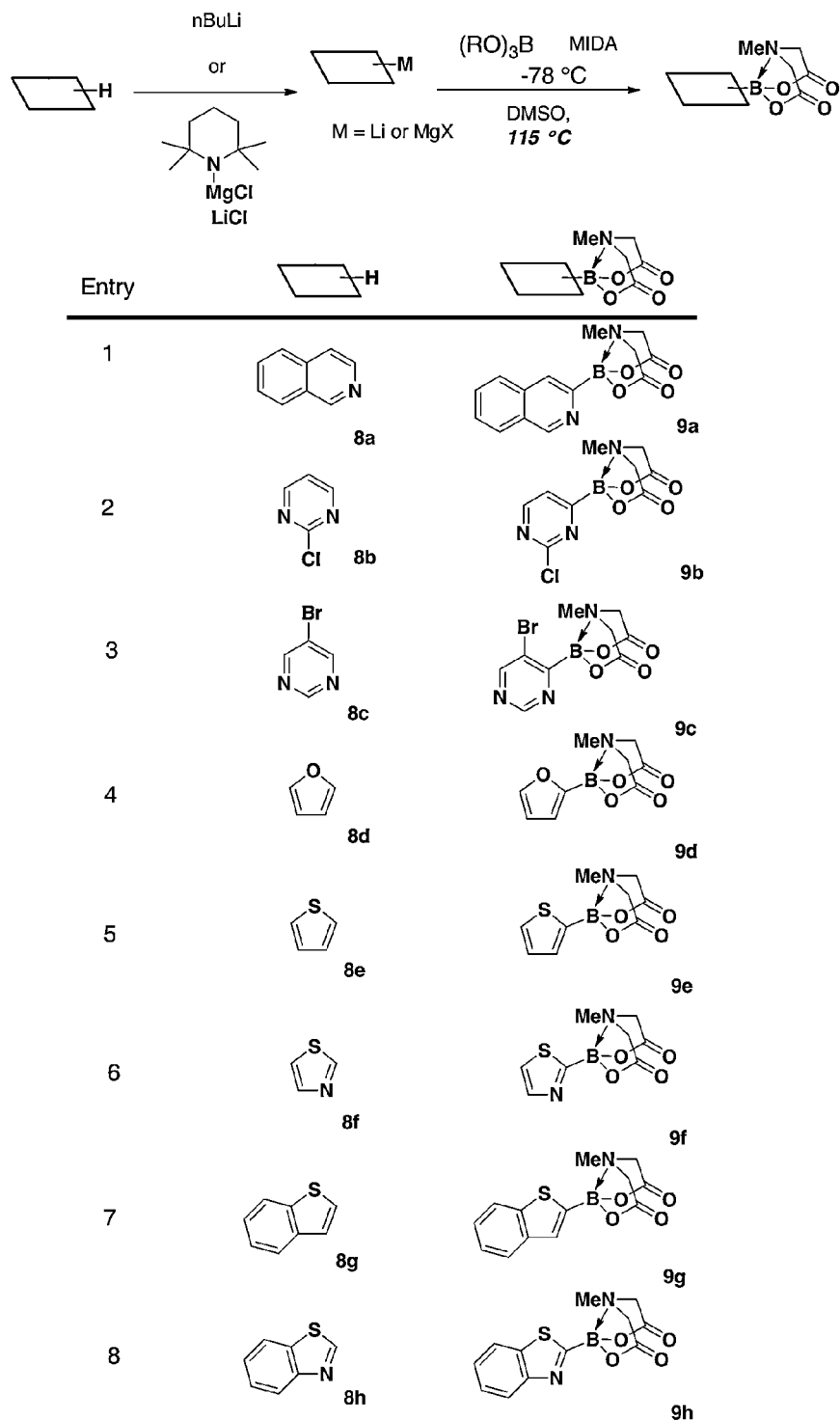
FIG. 5 represents chemical structures and reaction schemes for examples of the formation of protected organoboronic acids from various heterocyclic compounds.

FIG. 5 represents chemical structures and reaction schemes for examples of the formation of protected organoboronic acids 9a-9h from various heterocyclic compounds 8a-8h. The heterocyclic compounds 8a-8h are expected to react with MIDA in a polar aprotic solvent at a temperature of at least 100° C. to provide the corresponding protected organoboronic acids 9a-9h once the heterocyclic compounds have been transformed into the corresponding organoboronate salts.

The reagents used in the method of forming a protected boronic acid by reaction of an organoboronate salt with an imino-di-carboxylic acid can be obtained readily and at relatively low cost. The MIDA ligand can be prepared on the kilogram scale from the commodity chemicals iminodiacetic acid, formic acid, and formaldehyde, of which formic acid is the most expensive reagent. Moreover, MIDA is non-toxic, indefinitely air-stable, and biodegradable. The highly-crystalline and air-stable nature of MIDA boronates greatly facilitates their isolation, purification, and storage. Thus, the method of forming a protected boronic acid by reaction of an organoboronate salt with an imino-di-carboxylic acid may provide scalable and economical access to a wide range of 2-heterocyclic and other types of complex and/or important MIDA boronate building blocks.

In accordance with the present invention a second method of forming a protected boronic acid includes reacting in a reaction mixture a N-substituted morpholine dione, and an organoboronic acid represented by formula (XII):

$$R^1\text{—}B(OH)_2 \qquad (XII),$$

and forming a protected organoboronic acid represented by formula (III) in the reaction mixture:

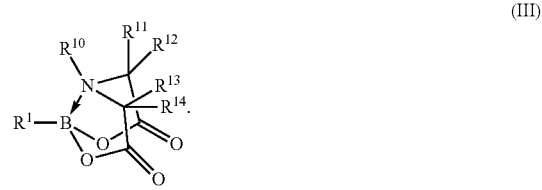

In formulas (III) and (XII), R$^1$ is an organic group as described above for formulas (I) and (III). In formula (III), R$^{10}$ is an organic group, and R$^{11}$, R$^{12}$, R$^{13}$ and R$^{14}$ independently are a hydrogen group or an organic group as described above for formula (III). The reaction mixture may include a polar aprotic solvent, and the reacting may includes maintaining the reaction mixture at a temperature of at most 100° C.

An example of the method of forming a protected boronic acid is represented in the following reaction scheme:

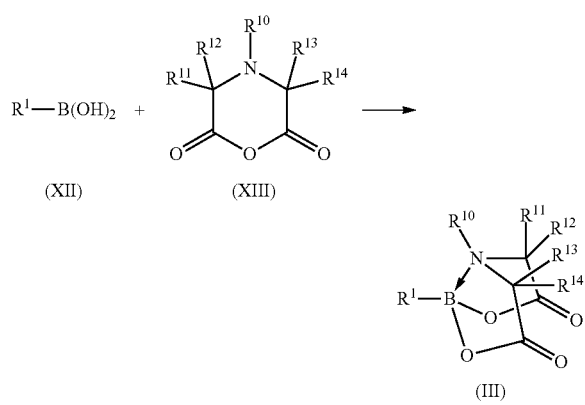

(XII)  (XIII)  (III)

where the compound represented by formula (XIII) is the N-substituted morpholine dione.

In one example, the organoboronic acid represented by formula (XII) is reacted with N-methyl morpholine dione, producing a protected organoboronic acid represented by formula (III) in which $R^{10}$ is methyl, and each of $R^{11}$, $R^{12}$, $R^{13}$ and $R^{24}$ is hydrogen. An example of this method is represented in the following reaction scheme:

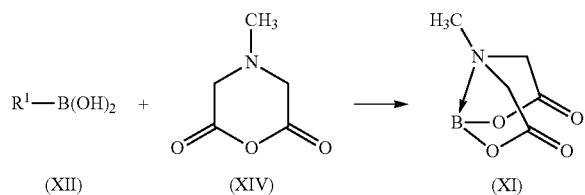

(XII)  (XIV)  (XI)

where the protected organoboronic acid is represented by formula (XI), and the N-methyl morpholine dione is represented by formula (XIV). The reagent N-methyl morpholine dione also is referred to herein as "MIDA anhydride", due to its similarity to the MIDA reagent and MIDA protecting group.

The reaction mixture includes a polar aprotic solvent. Examples of polar aprotic solvents include tetrahydrofuran (THF), dioxane, acetonitrile, dimethyl formamide (DMF), toluene and xylene. Preferably the reaction mixture includes THF.

The reacting includes maintaining the reaction mixture at a temperature of at most 100° C. Preferably the reacting includes maintaining the reaction mixture at a temperature of at most 90° C., preferably of at most 80° C. or at most 70° C. Preferably the reacting includes maintaining the reaction mixture at a temperature of from 40° C. to 100° C., more preferably from 50° C. to 90° C., and more preferably from 60° C. to 80° C.

In certain embodiments of the aforementioned methods, $R^{10}$ is methyl, and each of $R^{11}$, $R^{12}$, $R^{13}$ and $R^{14}$ is hydrogen.

In certain embodiments of the aforementioned methods, the polar aprotic solvent is selected from the group consisting of tetrahydrofuran (THF), dioxane, acetonitrile, dimethyl formamide (DMF), toluene and xylene.

In certain embodiments of the aforementioned methods, the reaction mixture is maintained at a temperature of from 40° C. to 100° C.

In certain embodiments of the aforementioned methods, $R^{10}$ is methyl, and each of $R^{11}$, $R^{12}$, $R^{13}$ and $R^{14}$ is hydrogen; and the polar aprotic solvent is selected from the group consisting of tetrahydrofuran (THF), dioxane, acetonitrile, dimethyl formamide (DMF), toluene and xylene.

In certain embodiments of the aforementioned methods, $R^{10}$ is methyl, and each of $R^{11}$, $R^{12}$, $R^{13}$ and $R^{14}$ is hydrogen; and the polar aprotic solvent is the polar aprotic solvent is THF.

In certain embodiments of the aforementioned methods, $R^{10}$ is methyl, and each of $R^{11}$, $R^{12}$, $R^{13}$ and $R^{14}$ is hydrogen; and the reaction mixture is maintained at a temperature of from 40° C. to 100° C.

In certain embodiments of the aforementioned methods, $R^{10}$ is methyl, and each of $R^{11}$, $R^{12}$, $R^{13}$ and $R^{14}$ is hydrogen; the polar aprotic solvent is selected from the group consisting of tetrahydrofuran (THF), dioxane, acetonitrile, dimethyl formamide (DMF), toluene and xylene; and the reaction mixture is maintained at a temperature of from 40° C. to 100° C.

In certain embodiments of the aforementioned methods, $R^{10}$ is methyl, and each of $R^{11}$, $R^{12}$, $R^{13}$ and $R^{14}$ is hydrogen; the polar aprotic solvent is selected from the group consisting of tetrahydrofuran (THF), dioxane, acetonitrile, dimethyl formamide (DMF), toluene and xylene; and the reaction mixture is maintained at a temperature of from 50° C. to 90° C.

In certain embodiments of the aforementioned methods, $R^{10}$ is methyl, and each of $R^{11}$, $R^{12}$, $R^{13}$ and $R^{14}$ is hydrogen; the polar aprotic solvent is selected from the group consisting of tetrahydrofuran (THF), dioxane, acetonitrile, dimethyl formamide (DMF), toluene and xylene; and the reaction mixture is maintained at a temperature of from 60° C. to 80° C.

In certain embodiments of the aforementioned methods, $R^{10}$ is methyl, and each of $R^{11}$, $R^{12}$, $R^{13}$ and $R^{14}$ is hydrogen; the polar aprotic solvent is tetrahydrofuran (THF); and the reaction mixture is maintained at a temperature of from 40° C. to 100° C.

In certain embodiments of the aforementioned methods, $R^{10}$ is methyl, and each of $R^{11}$, $R^{12}$, $R^{13}$ and $R^{14}$ is hydrogen; the polar aprotic solvent is tetrahydrofuran (THF); and the reaction mixture is maintained at a temperature of from 50° C. to 90° C.

In certain embodiments of the aforementioned methods, $R^{10}$ is methyl, and each of $R^{11}$, $R^{12}$, $R^{13}$ and $R^{14}$ is hydrogen; the polar aprotic solvent is tetrahydrofuran (THF); and the reaction mixture is maintained at a temperature of from 60° C. to 80° C.

Figure 6:
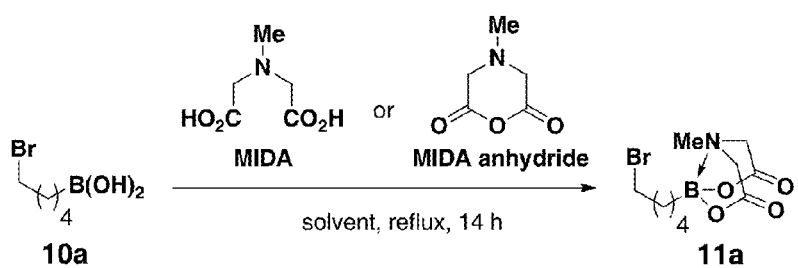
FIG. 6 represents chemical structures, reaction schemes and product yields for examples of the formation of 5-bromopentanyl MIDA boronate through two different synthetic methods.

FIG. 6 represents chemical structures, reaction schemes and product yields for examples of the formation of 5-bromopentanyl MIDA boronate 11a through two different synthetic methods. Simply heating a solution of 10a and MIDA anhydride (formula XIV) in THF for 14-24 hours produced an 88% yield of 11a (FIG. 6, entry 2). In contrast, reaction of 10a with MIDA using the conventional Dean-Stark conditions (PhMe:DMSO 10:1), resulted in substantial decomposition of the boronic acid, resulting in a low yield of 11a (FIG. 6, entry 1).

Figure 7:
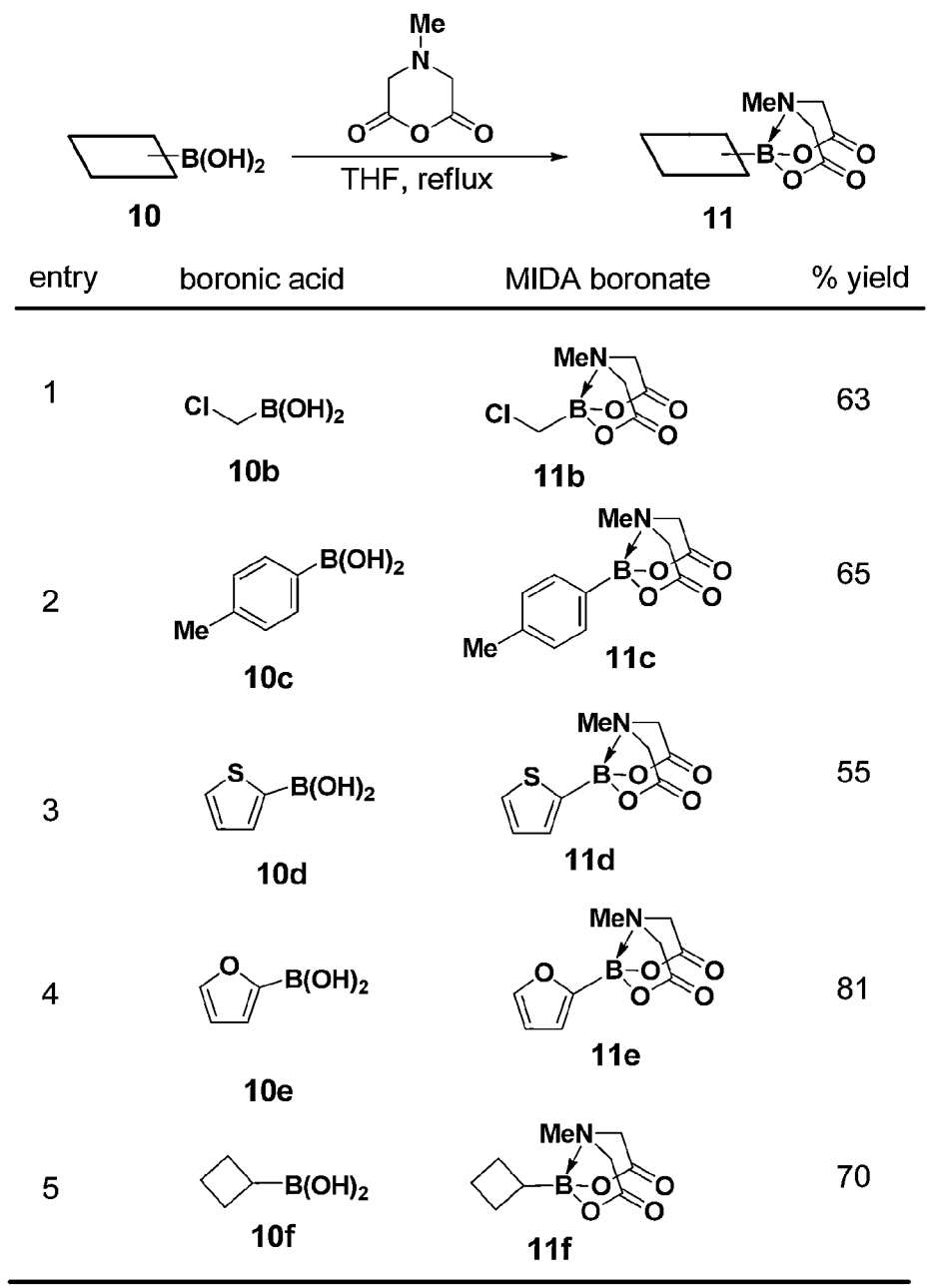
FIG. 7 represents chemical structures, reaction schemes and product yields for examples of the formation of protected organoboronic acids from various boronic acids, using MIDA anhydride.

FIG. 7 represents chemical structures, reaction schemes and product yields for examples of the formation of protected organoboronic acids 11a-11f from various boronic acids 10b-10f, using MIDA anhydride. The reaction of chloromethyl boronic acid 10b with MIDA under the conventional Dean-Stark conditions provided little to none of the desired product. In contrast, reacting 10b with MIDA anhydride provided the novel chloromethyl MIDA boronate 11b in good yield (FIG. 7, entry 1). The method of forming a protected boronic acid by reaction of an organoboronic acid with a N-substituted morpholine dione also was effective with aryl, heteroaryl, and cycloalkyl derivatives (FIG. 7, entries 2-5). It is expected that this method will be effective with a wide range of alkenyl boronic acids, and that it will be effective for boronic acids that are acid sensitive, such as Boc-protected pyrroles and indoles.

The reagents used in the method of forming a protected boronic acid by reaction of an organoboronic acid with a N-substituted morpholine dione can be obtained readily and at relatively low cost. The MIDA anhydride reagent is a colorless, air-stable, highly crystalline solid that can be prepared easily and can be purified by simple recrystallization on a scale of 100 g or more. MIDA anhydride is neutral and is more soluble than the MIDA reagent, and MIDA anhydride can be used to provide a protected organoboronic acid simply by refluxing the MIDA anhydride with the corresponding unprotected organoboronic acid, without the need for Dean-Stark dehydration.

Relative to the conventional Dean-Stark conditions using MIDA as a reagent, the method of forming a protected boronic acid by reaction of an organoboronic acid with a N-substituted morpholine dione can provide a convenient, mild, non-acidic and DMSO-free procedure for preparing a wide range of MIDA boronates. This remarkably simple method may provide efficient and economical access to a wide range of MIDA boronates from the corresponding readily-available boronic acids. Thus, the method has the potential to expand substantially the pool of MIDA boronates for potential applications in iterative cross-coupling, new building block syntheses, and slow release cross-coupling.

The protected organoboronic acids provided by either of the above methods are readily purified by column chromatography. This is a unique characteristic of MIDA boronate esters, as conventional organoboronic acids typically are unstable to chromatographic techniques. These protected organoboronic acids also may be crystalline, which can facilitate purification, utilization, and storage. These protected organoboronic acids are stable to long term storage, including storage on the bench top under air. This is also a unique characteristic of MIDA boronate esters, as many organoboronic acids are unstable to long term storage.

Figure 8:
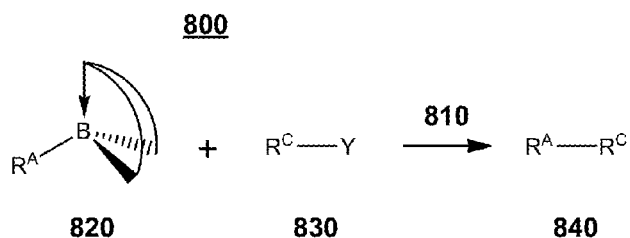
FIG. 8 represents a method of performing a cross-coupling reaction using a protected organoboronic acid.

FIG. 8 represents a method 800 of performing a chemical reaction, including reacting 810 a protected organoboronic acid 820 and an organohalide or organo-pseudohalide 830, to provide a cross-coupled product 840. $R^A$ and $R^C$ independently are organic groups, and Y is a halogen group or a pseudohalogen group. The reacting 810 may include contacting the protected organoboronic acid 820 and the organohalide or organo-pseudohalide 830 with a palladium catalyst in the presence of a base. The base may be a mild base, such as a base having a $pK_B$ of at least 1. The protecting group may be removed from the boron atom in situ, providing a corresponding unprotected organoboronic acid, which can then cross-couple with the organohalide or organo-pseudohalide 830. The protected organoboronic acid 820 includes a boron having an $sp^3$ hybridization and a conformationally rigid protecting group, and the organic group $R^A$ is bonded to the boron through a B—C bond. Preferably the protected organoboronic acid 820 includes a trivalent protecting group bonded to the boron.

The compound 830 with which the protected organoboronic acid 820 is reacted may be an organohalide or an organo-pseudohalide. The compound 830 may be an organohalide, which is an organic compound that includes at least one halogen group. Examples of halogen groups that may be present in an organohalide compound include —F, —Cl, —Br or —I. The compound 830 may be an organo-pseudohalide, which is an organic compound that includes at least one pseudohalogen group. Examples of pseudohalogen groups that may be present in an organo-pseudohalide compound include triflate (—O—S(=O)$_2$—CF$_3$), methanesulfonate (—O—S(=O)$_2$—CH$_3$), cyanate (—C≡N), azide (—N$_3$) thiocyanate (—N=C=S), thioether (—S—R), anhydride (—C(=O)—O—C(=O)—R), and phenyl selenide (—Se—C$_6$H$_5$). The halogen or pseudo-halogen group may be bonded to an alkyl group, a heteroalkyl group, an alkenyl group, a heteroalkenyl group, an alkynyl group, a heteroalkynyl group, an aryl group, a heteroaryl group, or a combination of at least two of these groups.

The compound 830 with which the protected organoboronic acid is reacted may be an organohalide or an organo-pseudohalide in which the halogen or pseudo-halogen group is bonded to an aryl group or a heteroaryl group. In one example, the compound is an unactivated aryl chloride or an unactivated heteroaryl chloride. Unactivated aryl chlorides, which do not contain any electron-withdrawing groups, typically react more slowly than aryl bromides or activated aryl chlorides in cross-coupling reactions.

The reaction mixture includes a base, and preferably the base has a $pK_B$ of at least 1. Preferably the base has a $pK_B$ of at least 1.5, more preferably of at least 2, more preferably of at least 3. Examples of bases having a $pK_B$ of at least 1 include bases that include an anion selected from $[PO_4]^{3-}$, $[C_6H_5O]^-$, $[CO_3]^{2-}$ and $[HCO_3]^{1-}$, such as alkali and alkaline earth salts of these anions. Specific examples of such bases include Li$_3$PO$_4$, Na$_3$PO$_4$, K$_3$PO$_4$, Li$^+$ [C$_6$H$_5$O]$^-$, Na$^+$ [C$_6$H$_5$O]$^-$, K$^+$[C$_6$H$_5$O]$^-$, Li$_2$CO$_3$, Na$_2$CO$_3$, K$_2$CO$_3$, MgCO$_3$, CaCO$_3$, LiHCO$_3$, NaHCO$_3$, and KHCO$_3$.

Preferably the reaction mixture includes a solvent. Examples of solvents include protic solvents such as water, methanol, ethanol, isopropyl alcohol (IPA) and butanol. Examples of solvents include aprotic solvents such as tetrahydrofuran (THF), dioxane, dimethyl formamide (DMF), toluene and xylene. The reaction mixture may include a mixture of two or more solvents, which independently may be a protic or aprotic solvent. Preferably the reaction mixture includes a protic solvent. A protic solvent may facilitate dissociation of the base in the reaction mixture.

The reaction mixture may include other ingredients, such as a copper-containing compound and/or a fluoride anion source. Examples of copper-containing compounds include CuI, CuCl and Cu(OAc)$_2$. Examples of fluoride anion sources include KF, NaF, and CsF.

Forming a cross-coupled product in the reaction mixture may include maintaining the reaction mixture at a temperature and for a time sufficient to form a cross-coupled product 840. For example, forming a cross-coupled product in the reaction mixture may include maintaining the reaction mixture at a temperature from 0° C. to 200° C. Preferably the forming includes maintaining the reaction mixture at a temperature from 25° C. to 150° C., and more preferably includes maintaining the reaction mixture at a temperature from 50° C. to 120° C. Forming a cross-coupled product in the reaction mixture may include maintaining the reaction mixture for a period of 1 hour to 100 hours. Preferably the forming includes maintaining the reaction mixture for a period of 2 hours to 72 hours, and more preferably includes maintaining the reaction mixture for a period of 4 hours to 48 hours. Preferably the forming a cross-coupled product in the reaction mixture includes maintaining the reaction mixture at a temperature from 25° C. to 150° C. for a period of 2 hours to 72 hours, and more preferably includes maintaining the reaction mixture at a temperature from 50° C. to 120° C. for a period of 4 hours to 48 hours.

The yield of cross-coupled product 840 in the reaction mixture may be at least 50%. Preferably the yield of cross-coupled product in the reaction mixture from this method is at least 60%. More preferably the yield of cross-coupled product in the reaction mixture from this method is at least 70%, more preferably is at least 75%, more preferably is at least 80%, more preferably is at least 85%, more preferably is at least 90%, more preferably is at least 95%, and more preferably is at least 99%.

The following examples are provided to illustrate one or more preferred embodiments of the invention. Numerous variations can be made to the following examples that lie within the scope of the invention.

EXAMPLES

General Methods

Commercial reagents were purchased from Sigma-Aldrich (St. Louis, Mo.), Fisher Scientific (Waltham, Mass.), Alfa Aesar/Lancaster Synthesis (Ward Hill, Mass.), TCI America (Portland, Oreg.), Frontier Scientific (Logan, Utah), Oakwood Products (West Columbia, S.C.) or Combi-Blocks (San Diego, Calif.) and were used without further purification unless otherwise noted. Solvents were purified via passage through packed columns as described by Pangborn and coworkers (Pangborn, A. B, et al. *Organometallics* 1996, 15, 1518-1520) (THF, Et$_2$O, CH$_3$CN, CH$_2$Cl$_2$: dry neutral alumina; hexane, benzene, and toluene, dry neutral alumina and Q5 reactant (copper(II) oxide on alumina); DMSO, DMF: activated molecular sieves). All water was deionized prior to use. Triethylamine, diisopropylamine, diethylamine, pyridine, and 2,6-lutidine were freshly distilled under an atmosphere of nitrogen from CaH$_2$. N-methyliminodiacetic acid was prepared according to procedures reported in the literature (Ballmer, S. G.; Gillis, E. P.; Burke, M. D. *Org. Syn.* 2009, 86, 344-359).

Unless otherwise noted, all reactions were performed in flame-dried glassware under argon. Organic solutions were concentrated via rotary evaporation under reduced pressure with a bath temperature of 20-60° C. Reactions were monitored by analytical thin layer chromatography (TLC) performed using the indicated solvent on E. Merck silica gel 60 F254 plates (0.25 mm). Compounds were visualized by exposure to a UV lamp (λ=254 or 366 nm) and/or treatment with a solution of KMnO$_4$, followed by brief heating with a Varitemp® heat gun (Master Appliance; Racine, Wis.).

Column chromatography was performed using standard methods (Still, 1978) or with a CombiFlash R$_f$ (Teledyne-Isco; Lincoln, Nebr.) purification system. Both methods were performed using Merck silica gel grade 9385 60 Å (230-400 mesh). For loading, compounds were adsorbed onto non acid-washed Celite 545 (approximately 10 g/mmol crude product) in vacuo from an acetone solution. Specifically, in each case the crude residue was dissolved/suspended in acetone and to the mixture was added Celite. The mixture was concentrated in vacuo to afford a free flowing powder which was then loaded on top of a silica gel column. To ensure quantitative transfer, this procedure was repeated with a small amount of acetone and Celite to transfer any remaining residue. MIDA boronates were compatible with standard silica gel chromatography, including standard loading techniques.

$^1$H-NMR spectra were recorded at 23° C. on a Varian Unity or a Varian Unity Inova 500 MHz spectrometer (Varian; Palo Alto, Calif.). Chemical shifts (δ) were reported in parts per million (ppm) downfield from tetramethylsilane and referenced to residual protium in the NMR solvent (CHCl$_3$, δ=7.26; CD$_2$HCN, δ=1.93, center line; acetone-d$_6$ δ=2.04, center line). Alternatively, NMR-solvents designated as "w/TMS" were referenced to tetramethylsilane (δ=0.00 ppm) added as an internal standard. Data were reported as follows: chemical shift, multiplicity (s=singlet, d=doublet, t=triplet, q=quartet, quint=quintet, sept=septet, m=multiplet, br=broad, app=apparent), coupling constant (J) in Hertz (Hz), and integration.

$^{13}$C NMR spectra were recorded at 23° C. on a Varian Unity 500 MHz spectrometer. Chemical shifts (δ) were reported in ppm downfield from tetramethylsilane and referenced to carbon resonances in the NMR solvent (CDCl$_3$, δ=77.0, center line; CD$_3$CN, δ=1.30, center line, acetone-d$_6$ δ=29.80, center line) or to added tetramethylsilane (δ=0.00). Carbons bearing boron substituents were not observed (quadrupolar relaxation).

$^{11}$B NMR spectra were recorded using a General Electric Unity Inova 400 MHz instrument and referenced to an external standard of (BF$_3$·Et$_2$O). High resolution mass spectra (HRMS) were performed by Furong Sun and Dr. Steve Mullen at the University of Illinois School of Chemical Sciences Mass Spectrometry Laboratory. Infrared spectra were collected from a thin film on NaCl plates or as KBr pellets on a Spectrum BX FT-IR spectrometer (Perkin-Elmer; Waltham, Mass.), a Mattson Galaxy Series FT-IR 5000 spectrometer or a Mattson Infinity Gold FT-IR spectrometer. Absorption maxima (v$_{max}$) were reported in wavenumbers (cm$^{-1}$).

Example 1

Preparation of Protected Organoboronic Acids from Corresponding Bromides

The general method for synthesizing protected organoboronic acids was as follows. A flame-dried, back-filled with argon 50 mL Schlenk Flask with septum and PTFE coated magnetic stirbar was charged with halide (1 eq), triisopropyl borate (1 eq), and THF (0.5 M). The flask was cooled with stirring to −78° C. nBuLi (1 eq) was added slowly down the side of the glass at a rate of 3 mmol every five minutes. After complete addition of the nBuLi, the reaction was stirred for one hour at −78° C. and three hours at 23° C. A second reaction apparatus was assembled while the first reaction was stirring. The apparatus, consisting of a 100 mL three-necked round bottom flask, 50 mL addition funnel, short path distillation apparatus, ground-glass jointed thermometer, 50 mL round bottom flask, PTFE coated magnetic stirbar, and two septa, was flame dried under vacuum and backfilled with argon. To the three necked round bottom flask was added MIDA (1.7 eq) and DMSO (0.85 M). The septum on the three-necked round bottom flask was subsequently replaced with a thermometer with PTFE adapter. The triisopropoxy borate salt solution prepared in the Schlenk flask was then transferred to the addition funnel using THF to affect a quantitative transfer. The septum on the addition funnel was then replaced with a ground glass stopper. A 145° C. oil bath was raised to the three necked round-bottom flask and water hoses were equipped to the short path distillation apparatus and the water was started. After the internal temperature of the apparatus reached 115° C., the addition of the triisopropoxy borate salt solution was started. The addition was monitored to ensure that the internal temperature was 110° C.-120° C. through modulation of the rate of addition. Approximate addition time was 45-60 minutes.

Following complete addition, the addition funnel was removed and replaced with a ground glass stopper, and the head temperature was allowed to drop to 50° C. The 145° C. oil bath was then dropped. The internal thermometer was removed and replaced with a ground glass stopper. The recovery flask was emptied and replaced. A second trap consisting of a cold-finger and a double-necked round bottom flask was equipped in series between the reaction apparatus and the vacuum manifold. A 50° C. oil bath was raised to the three-necked round bottom flask and a 250 mTorr vacuum was pulled on the chamber. DMSO was distilled until evidence of distillation ceased. The apparatus was then backfilled and the three necked round bottom was removed from the apparatus. The reaction was suspended using small amounts of acetonitrile. Celite was added and the resulting mixture was concentrated in vacuo to afford a free flowing powder. The mixture was placed under a high vacuum for twelve hours to remove residual DMSO. The reaction was loaded into a solid loading cartridge and an 80 g SiO$_2$ chromatographic column was run. An example of this method is depicted in the scheme below.

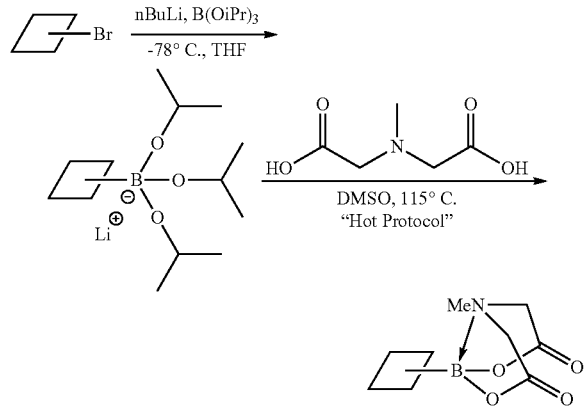

To form protected organoboronic acid 2-pyridyl MIDA boronate 2a, the general procedure was followed using 2-bromo pyridine (840 μL, 8.6 mmol), triisopropyl borate (2 mL, 8.6 mmol), THF (26 mL), DMSO (17 mL), nBuLi (3.44 mL, 2.5 M in hexanes), and N-methyliminodiacetic acid (2.15 g, 14.62 mmol). The mixture was eluted using 300 mL (95% Et$_2$O: 5% MeCN) followed by 100% MeCN until elution of product. The appropriate fractions were concentrated, azeotroped with DCM three times and placed under high vacuum for 20 minutes to afford 2-pyridyl MIDA boronate as an off-white crystalline solid (1.212 g, 59%). TLC (MeCN) R$_f$=0.26, visualized by UV (δ=254 nm) and KMnO$_4$ stain. $^1$H-NMR (500 MHz, CD$_3$CN) δ 8.67 (ddd, J=2.5, 1.5, 1.0 Hz, 1H), 7.70 (td, J=7.5, 1.5 Hz, 1H), 7.62 (dt, J=7.5, 1.0 Hz, 1H), 7.28 (ddd, J=8.5, 1.5 Hz, 1H), 8.67 (ddd, J=4.5, 1.5, 1.0 Hz, 1H), 4.09 (d, J=17 Hz, 2H), 3.98 (d, J=17 Hz, 2H), 2.55 (s, 3H). $^{13}$C-NMR (125 MHz, CD$_3$CN) δ 169.6, 150.8, 135.8, 128.1, 124.3, 62.9, 47.6. $^{11}$B-NMR (96 MHz, CD$_3$CN) δ 10.3. HRMS (CI+) Calculated for C$_{10}$H$_{12}$O$_4$N$_2$B (M+H)$^+$: 235.0890; Found: 235.0895. IR (KBr, cm$^{-1}$) 3004, 2956, 1774, 1749, 1633, 1590, 1466, 1340, 1289, 1279, 1214, 1152, 1095, 1054, 1045, 998, 964, 894, 866, 775, 754, 708, 683.

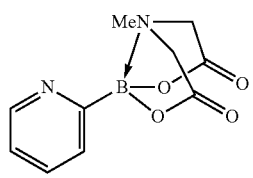

2a

To form protected organoboronic acid 6-methyl-2-pyridyl MIDA boronate 2b, the general procedure was followed using 2-bromo-6-methylpyridine (980 μL, 8.6 mmol), triisopropyl borate (2 mL, 8.6 mmol), nBuLi (3.44 mL, 2.5 M in hexanes), THF (26 mL), DMSO (17 mL), and N-methyliminodiacetic acid (2.15 g, 14.62 mmol). The mixture was eluted using an ethyl acetate and acetonitrile gradient (100% EtOAc→45% EtOAc: 55% MeCN). The appropriate fractions were concentrated, azeotroped with DCM three times and placed under high vacuum for 20 minutes to afford 2-pyridyl 6-methyl MIDA boronate as an off-white crystalline solid (1.243 g, 58%). $^1$H-NMR (500 MHz, CD$_3$CN) δ 7.57 (t, J=7.5 Hz, 1H), 7.40 (d, J=7.5, 1H), 7.14 (d, J=7.5 Hz, 1H), 4.07 (d, J=17 Hz, 2H), 4.00 (d, J=17 Hz, 2H), 2.55 (s, 3H), 2.48 (s, 3H).

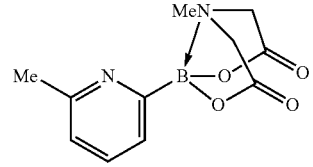

2b

To form protected organoboronic acid 5-methyl-2-pyridyl MIDA boronate 2c, the general procedure was followed using 2-bromo-5-methylpyridine (1.48 g, 8.6 mmol), triisopropyl borate (2 mL, 8.6 mmol), THF (26 mL), DMSO (17 mL), nBuLi (3.44 mL, 2.5 M in hexanes), and N-methyliminodiacetic acid (2.15 g, 14.62 mmol). The mixture was eluted using 300 mL (95% Et$_2$O: 5% MeCN) followed by 100% MeCN until elution of product. The appropriate fractions were concentrated, azeotroped with DCM three times and placed under high vacuum for 20 minutes to afford 5-methyl-2-pyridyl MIDA boronate as an off-white crystalline solid (1.09 g, 51%). $^1$H-NMR (500 MHz, CD$_3$CN) δ 8.53 (s, 1H), 7.53 (t, J=7.5, 2H), 4.07 (d, J=17 Hz, 2H), 3.96 (d, J=17 Hz, 2H), 2.53 (s, 3H), 2.31 (s, 3H).

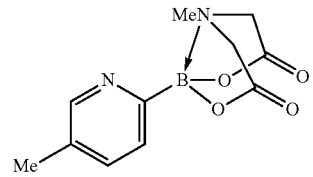

2c

To form protected organoboronic acid 4-methyl-2-pyridyl MIDA boronate 2d, the general procedure was followed using 2-bromo-4-methylpyridine (960 μL, 8.6 mmol), triisopropyl borate (2 mL, 8.6 mmol), THF (26 mL), DMSO (17 mL), nBuLi (3.44 mL, 2.5 M in hexanes), and N-methyliminodiacetic acid (2.15 g, 14.62 mmol). The mixture was eluted using 300 ml, (95% Et$_2$O: 5% MeCN) followed by 100% MeCN until elution of product. The appropriate fractions were concentrated, azeotroped with DCM three times and placed under high vacuum for 20 minutes to afford 4-methyl-2-pyridyl MIDA boronate as an off-white crystalline solid (897 mg, 42%). $^1$H-NMR (500 MHz, CD$_3$CN) δ 8.51 (d, J=5 Hz, 1H), 7.47 (s, 1H), 7.11 (d, J=5 Hz, 1H), 4.08 (d, J=17 Hz, 2H), 3.97 (d, J=17 Hz, 2H), 2.54 (s, 3H), 2.33 (s, 3H).

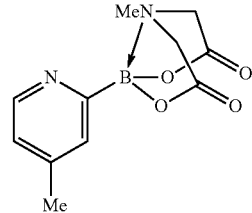

2d

To form protected organoboronic acid 6-methoxy-2-pyridyl MIDA boronate 2e, the general procedure was followed using 2-bromo-6-methoxypyridine (1.05 mL, 8.6 mmol), triisopropyl borate (2 mL, 8.6 mmol), THF (45 mL), DMSO (17 mL), nBuLi (3.44 mL, 2.5 M in hexanes), and N-methyliminodiacetic acid (2.15 g, 14.62 mmol). The mixture was eluted using an ethyl acetate and acetonitrile gradient. The concentrated product was suspended in 20 mL of MeCN and heated to 80° C. The solution was cooled to room temperature with stirring. The product was precipitated with a slow dropwise addition of 200 mL of Et$_2$O. The crystals were collected to afford 6-methoxy-2-pyridyl MIDA boronate as an off-white crystalline solid (1.83 g, 81%). ¹H-NMR (500 MHz, CD₃CN) δ 7.60 (dd, J=7 Hz, 8 Hz, 1H), 7.22 (d, J=7 Hz, 1H), 6.70 (d, J=8 Hz, 1H), 4.09 (d, J=16.5 Hz, 2H), 3.99 (d, J=16.5 Hz, 2H), 3.83 (s, 3H), 2.60 (s, 3H).

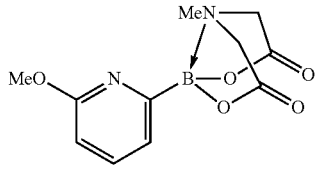

2e

To form protected organoboronic acid 6-trifluoromethyl-2-pyridyl MIDA boronate 2f, the general procedure was followed using 2-bromo-6-trifluoromethylpyridine (1.95 g, 8.6 mmol), triisopropyl borate (2 mL, 8.6 mmol), THF (26 mL), DMSO (17 mL), nBuLi (3.44 mL, 2.5 M in hexanes), and N-methyliminodiacetic acid (2.15 g, 14.62 mmol). The mixture was eluted using a hexanes and ethyl acetate gradient. The appropriate fractions were concentrated, azeotroped with DCM three times and placed under high vacuum for 20 minutes to afford 6-trifluoromethyl-2-pyridyl MIDA boronate as a tan crystalline solid (2.33 g, 90%). ¹H-NMR (400 MHz, CD₃CN) δ 7.95 (t, J=7.6 Hz, 1H), 7.87 (d, J=7.2 Hz, 1H), 7.72 (dd, J=7.6 Hz, 0.8 Hz, 1H), 4.13 (d, J=16.8 Hz, 2H), 3.98 (d, J=16.8 Hz, 2H), 2.57 (s, 3H).

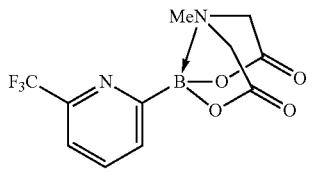

2f

To form protected organoboronic acid 5-trifluoromethyl-2-pyridyl MIDA boronate 2 g, the general procedure was followed using 2-bromo-5-trifluoromethylpyridine (1.94 g, 8.6 mmol), triisopropyl borate (2 mL, 8.6 mmol), THF (45 mL), DMSO (17 mL), nBuLi (3.44 mL, 2.5 M in hexanes), and N-methyliminodiacetic acid (2.15 g, 14.62 mmol). The mixture was eluted using an ethyl acetate and acetonitrile gradient. The concentrated product was suspended in 8 mL of MeCN and heated to 80° C. The solution was cooled to room temperature with stirring. The product was precipitated with a slow dropwise addition of 80 mL of Et₂O. The crystals were collected to afford 5-trifluoromethyl-2-pyridyl MIDA boronate as an off-white crystalline solid (1.45 g, 56%). ¹H-NMR (500 MHz, CD₃CN) δ 8.99 (s, 1H), 8.00 (dd, J=8 Hz, 1.5 Hz, 1H), 7.82 (d, J=8 Hz, 1H), 4.13 (d, J=17 Hz, 2H), 4.00 (d, J=17 Hz, 2H), 2.56 (s, 3H).

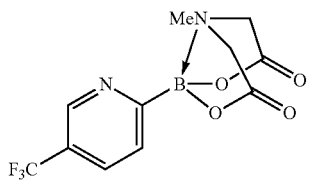

2g

To form protected organoboronic acid 4-trifluoromethyl-2-pyridyl MIDA boronate 2 h, the general procedure was followed using 2-bromo-4-trifluoromethyl-pyridine (1.06 mL, 8.6 mmol), triisopropyl borate (2 mL, 8.6 mmol), THF (17 mL), DMSO (60 mL), nBuLi (3.44 mL, 2.5 M in hexanes), and N-methyliminodiacetic acid (2.15 g, 14.62 mmol). One modification was made to the procedure. Instead of using THF to affect a quantitative transfer of the triisopropoxyborane salt, 43 mL of DMSO was used. The mixture was eluted using 300 mL (95% Et₂O: 5% MeCN) followed by 300 mL (75% Et₂O: 25% MeCN) and (50% Et₂O: 50% MeCN) until elution. The concentrated product was suspended in 5 mL of MeCN and heated to 80° C. The solution was cooled to room temperature with stirring. The product was precipitated with a slow dropwise addition of 50 mL of Et₂O. The crystals were collected and the same precipitation was performed a second time to afford 4-trifluoromethyl-2-pyridyl MIDA boronate as an off-white crystalline solid (1.35 g, 53%). ¹H-NMR (500 MHz, CD₃CN) δ 8.92 (d, J=5 Hz, 1H), 7.86 (s, 1H), 7.57 (d, J=5 Hz, 1H), 4.13 (d, J=17 Hz, 2H), 4.00 (d, J=17 Hz, 2H), 2.56 (s, 3H).

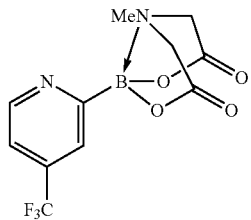

2h

To form protected organoboronic acid 6-bromo-2-pyridyl MIDA boronate 2l, the general procedure was followed using 2,6-dibromopyridine (2.04 g, 8.6 mmol), triisopropyl borate (2 mL, 8.6 mmol), THF (26 mL), DMSO (17 mL), nBuLi (3.44 mL, 2.5 M in hexanes), and N-methyliminodiacetic acid (2.15 g, 14.62 mmol). The mixture was eluted using a hexanes and ethyl acetate gradient (25% hexanes: 75% EtOAc→100% EtOAc). The concentrated product was suspended in 17 mL of acetone and was precipitated with a slow dropwise addition of 170 mL of hexanes. The crystals were collected to afford 6-bromo-2-pyridyl MIDA boronate as a white crystalline solid (1.46 g, 54%). ¹H-NMR (400 MHz, CD₃CN) δ 7.62 (dt, J=3.2, 6 Hz, 2H), 7.49 (dt, J=3.2, 11.5 Hz, 1H), 4.10 (d, J=16.8 Hz, 2H), 3.96 (d, J=16.8 Hz, 2H), 2.58 (s, 3H).

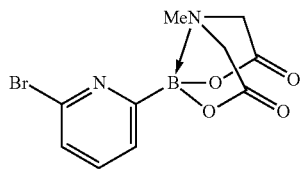

2i

To form protected organoboronic acid 2-pyrazinyl MIDA boronate 5a, the general procedure was followed using 2-bromo pyrazine (275 μL, 3.0 mmol), triisopropyl borate (690 μL, 3.0 mmol), THF (11 mL), DMSO (6 mL), nBuLi (1.2 mL, 2.5 M in hexanes), and N-methyliminodiacetic acid (750 mg, 5.1 mmol). The mixture was eluted using 300 mL (95% Et₂O: 5% MeCN) followed by 100% MeCN until elution of product. The appropriate fractions were concentrated, azeotroped with DCM three times and placed under high vacuum for 20 minutes to afford 2-pyrazinyl MIDA boronate as an orange crystalline solid (300 mg, 43%). ¹H-NMR (500 MHz, CD₃CN) δ 8.77 (d, J=1.5 Hz, 1H), 8.70 (t, J=1.5 Hz 1H), 8.53 (d, J=2.5 Hz, 1H), 4.13 (d, J=17 Hz, 2H), 3.98 (d, J=17 Hz, 2H), 2.59 (s, 3H).

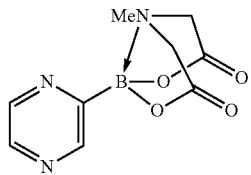

5a

To form protected organoboronic acid 5-thiazolyl MIDA boronate 5e, the general procedure was followed using 5-bromothiazole (760 μL, 8.6 mmol), triisopropyl borate (2 mL, 8.6 mmol), THF (26 mL), DMSO (17 mL), nBuLi (3.44 mL, 2.5 M in hexanes), and N-methyliminodiacetic acid (2.15 g, 14.62 mmol). The mixture was eluted using an ether and acetonitrile gradient. The appropriate fractions were concentrated. The mixture was then suspended in 5 mL of acetonitrile and heated to 80° C. with stirring and then cooled to room temperature. The mixture was diluted with 20 mL of DCM then with stirring 60 mL of Ether was added dropwise over 1 hour. The off-white crystalline solid was filtered then washed through the frit into a clean round bottom flask. The resulting solution was concentrated then azeotroped three times with a 50:50 Ether:DCM mixture. The resulting crystalline solid was placed under a high vacuum for 20 minutes to afford 5-thiazolyl MIDA boronate 5e as an off-white crystalline solid (337 mg, 44%). $^1$H-NMR (500 MHz, $CD_3CN$) δ 9.03 (s, 1H), 7.98 (s, 1H), 4.10 (d, J=17 Hz, 2H), 3.93 (d, J=17 Hz, 2H), 3.73 (s, 3H). $^{13}$C-NMR (125 MHz, $CD_3CN$) δ 168.8, 158.1, 150.0, 62.6, 48.5.

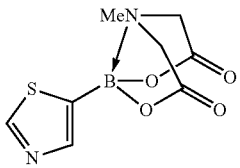

Example 2

Preparation of Ethynyl MIDA Boronate from Corresponding Grignard Reagent

To an oven-dried 5000-mL 3-neck round-bottomed flask equipped with a magnetic stir bar, a 500-mL pressure-equalizing addition funnel, and two rubber septa was added THF (750 mL) and trimethyl borate (61 mL, 550 mmol, 1.1 equiv) under an atmosphere of Ar(g). The solution was cooled to 78° C. in a dry ice/IPA bath. The addition funnel was charged with the first portion of ethynal magnesium bromide solution (500 mL, 250 mmol, 0.50 M in THF) and added drop-wise over 35 min. The addition funnel was charged with the second portion of ethynal magnesium bromide solution (500 mL, 250 mmol, 0.50 M in THF) and added drop-wise over 30 min. The reaction vessel was removed from the bath and allowed to warm to ambient temperature over the course of 3 h resulting in a thick white slurry. While the slurry of the "ate" complex was warming to ambient temperature, an oven-dried 3000-mL 3-neck round-bottomed flask equipped with a magnetic stir bar, a thermometer, a septum, and a distillation train was charged with MIDA (162 g, 1100 mmol, 2.2 equiv), DMSO (750 mL) and toluene (300 mL). Using a heating mantle and variac, the suspension was brought to an internal temp of 120° C. and the $H_2O$/toluene azeotrope distilled off (head temperature of 82-87° C.) resulting in a homogeneous light-orange solution. The internal temperature of the solution was raised to 140° C. and the suspension of the "ate" complex was added over the course of 4 h via cannula transfer (Teflon® cannula, inner diameter=4 mm) under a positive pressure of Ar(g) at a rate such that the internal temperature remained between 120-160° C.

After the addition was completed the reaction vessel was washed with THF (2×60 mL) and the washes added via cannula transfer to the reaction vessel containing the MIDA solution. The remaining THF and MeOH were allowed to distill off (~15 min) followed by vacuum distillation of the DMSO. The reaction vessel was allowed to cool to ambient temperature and acetone was added (1.5 L) with manual and mechanical agitation. Overnight agitation of this mixture resulted in a thick brown slurry that was filtered and the collected brown solids were washed with acetone (3×300 mL). The filtrate was concentrated under reduced pressure to afford a thick black oil that was cooled to 0° C. in an ice-bath and treated with brine (500 mL) for 30 min with vigorous stirring. The resulting brown precipitate was collected by suction filtration affording the crude MIDA boronate. Semi-purification by chromatography followed by treatment of the crude MIDA boronate with charcoal in acetone provided a yellow oil after concentration under reduced pressure. The crude oil was dissolved in a minimal amount of acetone and $Et_2O$ was added to precipitate the MIDA boronate 7a as a white solid that was collected by suction filtration and washed with $Et_2O$ (crop 1=41.0 g, crop 2=4.5 g) to provide the title compound as an off white powder in 50% yield.

Example 3

Preparation of Propynyl MIDA Boronate from Corresponding Grignard Reagent

To a 300 mL 3-neck round bottom flask equipped with a stir bar was added $B(OMe)_3$ (5.9 mL, 53 mmol) and THF (50 mL). The solution was cooled to −78° C. Propynylmagnesium bromide (0.5 M in THF, 100 mL, 50 mmol) was added dropwise via cannula over 45 min. The resulting solution was stirred at −78° C. for 1.5 hr, followed by stirring at 23° C. for 2 hr. In a separate 500 mL 3-neck round bottom flask equipped with a stir bar, internal thermometer, 500 mL addition funnel, and distillation apparatus was added MIDA (15.0 g, 102 mmol) and DMSO (50 mL). The solution was heated with an oil bath to an internal temperature of 110-115° C. The borate suspension was transferred to the addition funnel and was continuously agitated with a stream of nitrogen. The borate solution was added dropwise to the hot MIDA solution over 2 hr 50 min, keeping the internal temperature between 105 and 115° C.

After full addition of the borate solution, the reaction solution was cooled to 60° C. and placed under vacuum (300 mtorr) to distill the reaction to dryness. The resulting foam was cooled to room temperature and dissolved in 200 mL EtOAc, 50 mL acetone, and 75 mL $H_2O$ and poured into 200 mL EtOAc:Acetone (1:1) and 75 mL brine. The mixture was shaken and the aqueous layer was removed and extracted with EtOAc (1×100 mL). The combined organic phases were washed with brine (2×20 mL). The brine wash was back extracted with EtOAc:Acetone (2:1, 1×75 mL) The combined organic phases were dried over $MgSO_4$, filtered, and concentrated in vacuo. The resulting yellow solid was dissolved in 100 mL THF and 1000 mL $Et_2O$ was added to precipitate the product. The resulting solid was collected by vacuum filtration to yield propynyl MIDA boronate 7b as a white solid (7.48 g, 77%).

Example 4

Preparation of Vinyl MIDA Boronate from Corresponding Grignard Reagent

To a dry 500 mL Schlenk flask equipped with a stir bar was added THF (100 mL) and B(OMe)3 (11.7 mL, 105 mmol). The solution was cooled via a −78° C. cold bath. To the solution was added via cannula over 5 min. vinylmagnesium bromide as a solution in THF (1.0 M, 100 mL, 100 mmol). The resulting mixture was stirred for 2 h, then the cold bath was removed and the mixture was allowed to warm to room temperature with stirring for 2 h. The beige mixture was transferred to a 250 mL pressure-equalizing addition funnel.

A 3-neck 500 mL round bottom flask equipped with a stir bar was charged with DMSO (100 mL), N-methyliminodiacetic acid (29.5 g, 200 mmol) and toluene (50 mL). To the necks of the round bottom were fitted the addition funnel, a thermometer, and a std. distillation apparatus. The mixture was heated to an internal temperature of 115° C. upon which the THF mixture was added via the addition funnel at a rate to maintain an internal temperature between 95-110° C. During this time the THF is distilled away from the hot DMSO mixture. Upon completion of the addition and after the internal temperature had risen to 120° C. the distillation pot was allowed to cool to room temperature.

The DMSO mixture was diluted with acetone (300 mL) and the resulting mixture was filtered through a pad of Celite. The collected solids were extracted with acetone (100 mL) and the combined filtrate was concentrated in vacuo to afford a DMSO solution. The DMSO solution was distilled to near dryness (1 Torr, 100° C.). The remaining solids were dissolved in acetone:water (100 mL:100 mL) and were transferred to a 1000 mL separatory funnel. The solution was diluted with brine (100 mL) and EtOAc (200 mL). The mixture was shaken and the phases were separated. The aq. phase was twice extracted with acetone:EtOAc (100 mL:200 mL). The combined organics were washed with brine (3×100 mL). The combined brine washes were back-extracted with EtOAc (100 mL). The combined organics were dried over MgSO4, filtered, then concentrated in vacuo to afford an off-white solid which was then recrystallized from acetone (100 mL) diluted with Et2O (2000 mL) to afford the product 7c as an off-white solid (9.95 g, 54%).

Example 5

Preparation of Propynyl MIDA Boronate by Direct Deprotonation

To a dry 50 mL graduated Schlenk tube cooled in a −78° C. bath was added in small portions 1-butyne gas until 12 mL of 1-butyne (150 mmol) had condensed in the flask. Separately, a dry 200 mL Schlenk flask equipped with a stir bar was charged with THF (100 mL) and n-BuLi (2.5 M in hexanes, 40 mL, 100 mmol), and then cooled via a −78° C. bath. To the n-BuLi solution was added in small portion the liquid butyne at a rate necessary to keep the internal temperature below −45° C. Following the addition, the solution was stirred for 1 h at an internal temp of −65° C. Separately, a dry 500 mL 3-neck flask equipped with a stir bar was charged with THF (50 mL) and B(OMe)$_3$ (11.1 mL, 100 mmol), then cooled to an internal temp of −65° C. To the B(OMe)$_3$ solution was added via cannula the alkyne solution. Following the addition, the solution was allowed to warm to room temperature with stirring over 2 h. Separately, a 300 mL 3-neck flask equipped with a large stir bar was charged with DMSO (100 mL) and N-methyliminodiacetic acid (23.87 g, 160 mmol). The flask was fitted with a thermometer and a standard distillation apparatus. The DMSO mixture was heated to an internal temperature of 110° C., upon which to the mixture was added via cannula the borate solution at a rate necessary to maintain an internal temperature of 95-115° C.

Following the addition, residual THF was distilled at 30 Torr, then DMSO was reduced to a minimum via distillation at 1 Torr. The resulting mixture was transferred to a 1000 mL separatory funnel using acetone (100 mL) and water (100 mL). The mixture was diluted with brine (100 mL), then extracted with EtOAc (200 mL). The aq. phase was extracted with acetone:EtOAc (100 mL:200 mL). The combined organics were washed with water (2×200 mL), then brine (2×50 mL). The combined aqueous washes were back-extracted with EtOAc (3×100 mL). The combined organics were dried over MgSO$_4$, filtered, and then concentrated in vacuo. The product was recrystallized by dissolving the residue in a minimum volume of acetone and then layering the solution with Et$_2$O (1.5 L) and allowing to stand for 24 h. The resulting crystals were collected via filtration to afford the pure product as a colorless, crystalline solid, 4.05 g (19%). $^1$H-NMR (acetone-d6, 500 MHz): 4.23 (d, J=17.0 Hz, 2H), 4.05 (d, J=17 Hz, 2H), 3.19 (s, 3H), 2.21 (q, J=7.5 Hz, 2H), 1.11 (t, J=7.5 Hz, 3H).

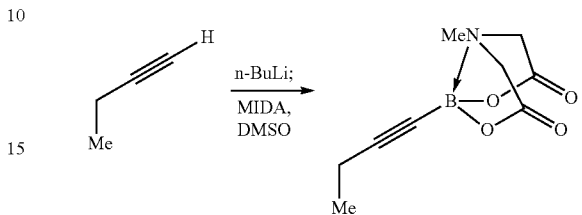

Example 6

Preparation of MIDA Anhydride

A round-bottom flask equipped with a PTFE-coated magnetic stir bar was charged with N-methyliminodiacetic acid (25.0 g, 170 mmol, 1.0 equiv), acetic anhydride (85 mL, ~850 mmol, ~5 equiv.), and pyridine (274.9 µL, 3.4 mmol, 0.02 equiv). The flask was capped with a rubber septum which was pierced with an 18 gauge needle (alternatively a reflux condenser could be used). The reaction was lowered into a pre-heated 70° C. oil bath and stirred until the mixture became clear and dark orange (about 1.5 h). The acetic acid, pyridine, and remaining acetic anhydride were then removed by vacuum distillation (37° C. to 42° C. at 30 Torr). The resulting brown-black liquid was azeotroped three times with toluene (50 mL) to remove residual acetic acid and then transferred to an Erlenmeyer flask. To this flask was added enough diethyl ether to dissolve the crude N-methyl morpholine dione product (~400 mL). The resulting mixture was filtered to remove a black-brown precipitate, and the filtrate was concentrated in vacuo. The resulting pale yellow solid was then recrystallized from a minimum amount of hot diethyl ether to yield N-methyl morpholine dione (MIDA anhydride; 16.9 g, 131 mmol, 77%) as an off-white crystalline solid.

Example 7

Preparation of Protected Organoboronic Acids from Corresponding Boronic Acids Using MIDA Anhydride The general method for synthesizing protected organoboronic acids was as follows. A flame-dried 20 mL i-chem vial equipped with a PTFE-coated magnetic stir bar was charged with boronic acid (1 mmol, 1 equiv.) and MIDA anhydride (2.5-5 mmol, 2.5-5 equiv.). The vial was capped with a PTFE-lined septum cap, evacuated and backfilled with argon three times. To this vial was added 5 mL dry THF through syringe. The vial was lowered into a pre-heated 70° C. aluminum heat block, where the reaction stirred for 14-24 h. The vial was then removed from the heating source and allowed to cool to room temperature. The solution was transferred to a 125 mL separatory funnel with 5 mL diethyl ether followed by 15 mL deionized water. The phases are separated and the aqueous layer is extracted four times with 15 mL 1:1 diethyl ether: THF. The combined organics are washed with 30 mL saturated NaCl, dried over magnesium sulfate, and concentrated in vacuo.

To form protected organoboronic acid chlormethyl MIDA boronate 11b, the general procedure was followed. To a 7 mL vial equipped with a stir bar was added chloromethylboronic acid (102.5 mg, 1.1 mmol, 1.0 eq), MIDA anhydride (345.4 mg, 2.7 mmol, 2.5 eq), and dry THF (2 mL, 0.5 M). The vial was flushed with nitrogen and the sealed vial was placed in a 70° C. heating block. After 30 min. the reaction solution was cooled to room temperature and filtered through a plug of celite, eluting with acetone. The solution was concentrated in vacuo. The residue was dissolved in acetone and precipitated from solution with Et$_2$O. The white solid was collected by vacuum filtration to afford chloromethyl MIDA boronate (140.5 mg, 63%).

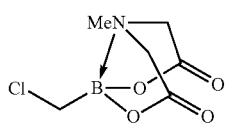
11b

While various embodiments of the invention have been described, it will be apparent to those of ordinary skill in the art that other embodiments and implementations are possible within the scope of the invention. Accordingly, the invention is not to be restricted except in light of the attached claims and their equivalents.

Example 8

Preparation of Iodopolyenyl MIDA Boronates

Figure 9:
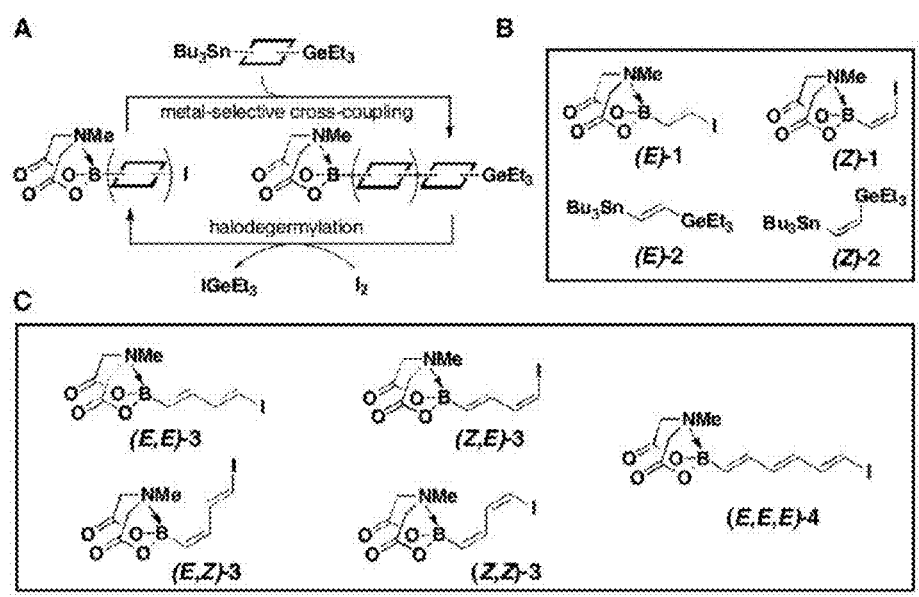
FIGS. 9A-C: A. A strategy for ICC of halogen-masked bifunctional building blocks. B. Core building blocks to enable general access to stereoisomeric iodopolyenyl MIDA boronates. C. Iodo-polyenyl MIDA boronates for the synthesis of natural products.

This example presents a strategy for preparing iodopolyenyl MIDA boronates via the iterative cross coupling (ICC) of iodo-masked bifunctional building blocks. As shown in FIG. 9, the approach involves metal-selective cross-coupling of Sn/Ge bis-metallated olefins to generate polyenylgermanium intermediates followed by stereospecific iododegermylations. To the best of our knowledge, iododegermylations of polyenylgermanium species were unreported. We hypothesized that iterative cycles of metal-selective coupling/iododegermylation with core building blocks 1 and 2 (FIG. 9B) could provide access to iodo-polyenyl MIDA boronates in all possible stereoisomeric forms (FIG. 9C).

Figure 10:
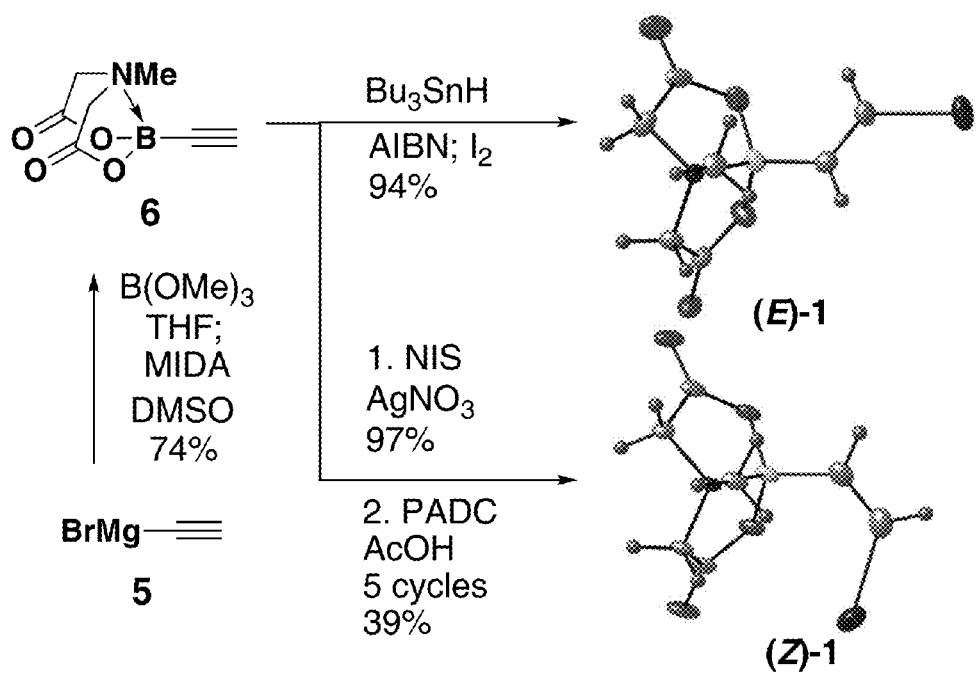
FIG. 10 depicts the synthesis of bifunctional MIDA boronate building blocks (E)-1 and (Z)-1 from the common intermediate ethynyl MIDA boronate.

We discovered that (E)-1 and (Z)-1 can both be generated from ethynyl MIDA boronate 6, which in turn can be prepared from readily-available Grignard reagent 5. Specifically, as shown in FIG. 10, the addition of 5 to trimethyl borate followed by direct transligation of the resulting magnesium ate complex with MIDA generated 6 as a colorless, crystalline solid. When this transligation was executed at 115° C., a good yield of 6 was achieved on the decagram scale. Although 6 is fully compatible with silica gel chromatography, this highly versatile building block can also be conveniently isolated in excellent purity via recrystallization. One-pot hydrostannylation of 6 followed by iododestannylation of the resulting bis-metallated intermediate provided an excellent yield of (E)-1. Alternatively subjecting 6 to a series of silver-promoted alkyne iodination followed by PADC-mediated semireduction provided the complementary building block (Z)-1. Importantly, both (E)-1 and (Z)-1 are air- and chromatographically-stable, highly crystalline free-flowing solids.

Figure 11:
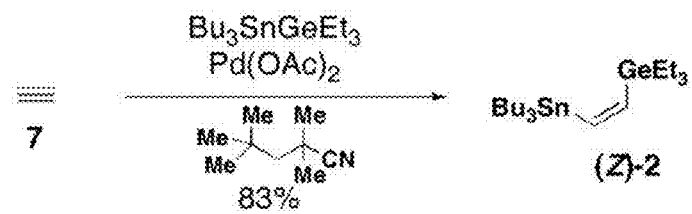
FIG. 11 depicts the stereocontrolled preparation of (Z)-2.

A synthesis of (E)-2 has been previously reported, but a stereocontrolled route to (Z)-2 was unknown. (F. David-Quillot, J. Thibonnet, D. Marsacq, M. Abarbri, A. Duchene, *Tetrahedron Lett.* 2000, 41, 9981-9984) As shown in FIG. 11, hybridizing methodology previously reported for the germyl-stannylation of substituted alkynes and the silyl-stannylation of acetylene core building block (Z)-2 was efficiently prepared as a single stereoisomer via the palladium-mediated cis-germyl-stannylation of acetylene gas.

Figure 12:
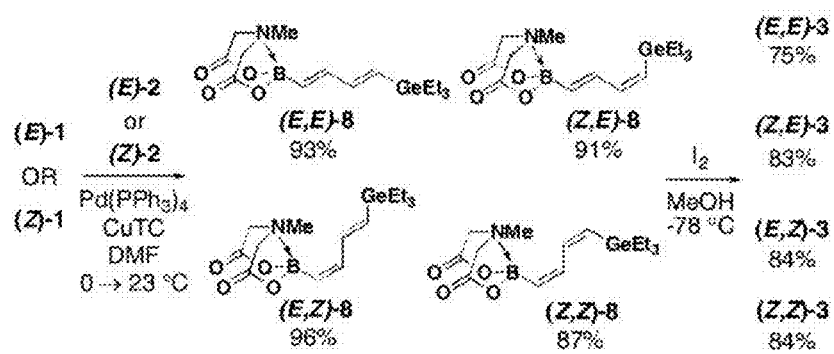
FIG. 12 depicts the efficient and stereospecific syntheses of all possible stereoisomers of 3 via metal-selective ICC.
Figure 13:
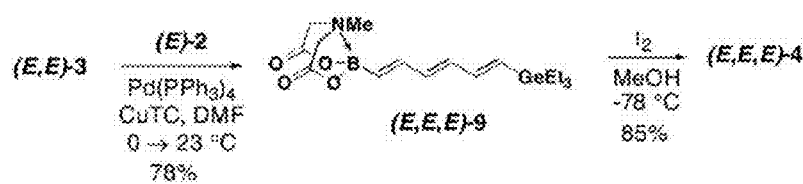
FIG. 13 depicts the preparation of iodotrienyl MIDA boronate (E,E,E)-4 via metal-selective ICC.

With these four core building blocks in hand, we sought general conditions for efficient cycles of stereospecific metal-selective couplings and iododegermylations (FIG. 9A). As shown in FIG. 12, we found that Liebeskind-type conditions are remarkably effective for the targeted metal-selective Stille couplings. In fact, using the exact same set of very mild conditions [Pd(PPh)$_4$/CuTC, DMF, 0° C. to 23° C.], all possible combinations of 1 and 2 were stereospecifically coupled in excellent yields to generate dienylgermanium intermediates 8. Completing the envisioned cycle, stereospecific iododegermylations of all four of these intermediates were readily achieved via treatment with I$_2$ in MeOH at −78° C., thereby providing all of the targeted iododienyl MIDA boronate building blocks 3 in good yields and as single stereoisomers. Harnessing the iterative nature of this strategy, the more advanced trienyl halide, (E,E,E)-4 was also readily prepared via simply executing an additional cycle of metal-selective coupling and stereospecific iododegermylation (FIG. 13).

As shown in Table 1 below, these bifunctional building blocks collectively enable the preparation of a broad range of stereochemically complex polyene natural product frameworks. After surveying a variety of catalysts, bases, and solvents we found a very mild set of Buchwald-type cross-coupling conditions [Pd(OAc)$_2$, SPhos or XPhos, Cs$_2$CO$_3$, THF, 23° C.] that proved to be highly effective. Specifically, all possible stereoisomers of 1 and 3 were cross-coupled with both (E)- and (Z)-pentenyl boronic acid 10 in good to excellent yields and with outstanding levels of stereoretention. Observations of complete stereoretention even when coupling the sterically encumbered MIDA boronate (Z)-1 (entries 2 and 8) and preparing the very challenging (Z,Z,Z)-triene 22 (entry 10) are particularly notable. Collectively, products 11-22 represent all possible stereoisomers of the core dienyl- and trienyl substructures that appear in a wide range of natural products derived from all major biosynthetic pathways. Importantly, these products all retain the potential for subsequent cross-coupling reactions upon hydrolysis of the MIDA boronate functional group with mild, aqueous base.

TABLE 1

[a]Stereospecific Suzuki-Miyaura Cross-Couplings yielding all possible stereoisomers of di- and trienyl MIDA boronates.

| entry | boronic Acid | iodoalkenyl MIDA boronate | product | % yield |
|---|---|---|---|---|
| 1 | Me~~~B(OH)$_2$ (E)-10 | (E)-1 | 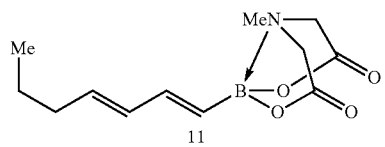 11 | 95 |

TABLE 1-continued

*Stereospecific Suzuki-Miyaura Cross-Couplings yielding all possible stereoisomers of di- and trienyl MIDA boronates.

| entry | boronic Acid | iodoalkenyl MIDA boronate | product | % yield |
|---|---|---|---|---|
| 2 | (E)-10 | (Z)-1 | 12 | 77 |
| 3 | (E)-10 | (E,E)-3 | 13 | 75 |
| 4 | (E)-10 | (E,Z)-3 | 14 | 78 |
| 5 | (E)-10 | (Z,E)-3 | 15 | 87 |
| 6 | (E)-10 | (Z,Z)-3 | 16 | 64 |
| 7 | (Z)-10 | (E)-1 | 17 | 91 |
| 8 | (Z)-10 | (Z)-1 | 18 | 74 |
| 9 | (Z)-10 | (E,E)-3 | 19 | 77 |

TABLE 1-continued

*Stereospecific Suzuki-Miyaura Cross-Couplings yielding all possible stereoisomers of di- and trienyl MIDA boronates.

| entry | boronic Acid | iodoalkenyl MIDA boronate | product | % yield |
|---|---|---|---|---|
| 10 | (Z)-10 | (E,Z)-3 | 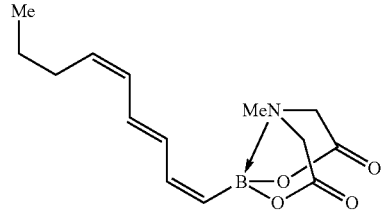 20 | 84 |
| 11 | (Z)-10 | (Z,E)-3 | 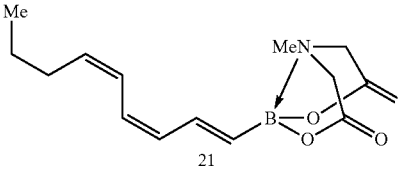 21 | 82 |
| 12 | (Z)-10 | (Z,Z)-3 | 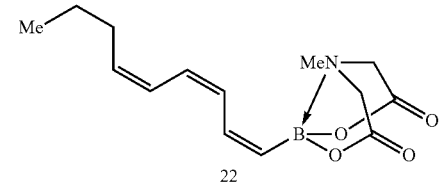 22 | 62 |

$^a$1.0 equiv. 1 or 3, 1.5 equiv. 10, Pd(OAc)$_2$, SPhos (entries 1, 3, 4, 7, 9, 10) or XPhos (entries 2, 5, 6, 8, 11, 12), Cs$_2$CO$_3$, THF, 23° C.

Example 9

Preparation of Propynyl MIDA Boronate

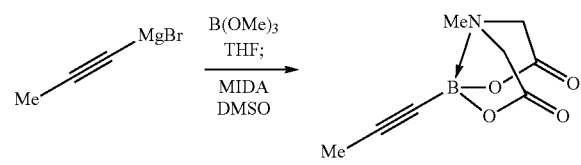

To a 300 mL 3-neck round bottom flask equipped with a stir bar was added B(OMe)$_3$ (5.9 mL, 53 mmol) and THF (50 mL). The solution was cooled to −78° C. Propynylmagnesium bromide (0.5 M in THF, 100 mL, 50 mmol) was added dropwise via cannula over 45 min. The resulting solution was stirred at −78° C. for 1.5 hr, followed by stirring at 23° C. for 2 hr. In a separate 500 mL 3-neck round bottom flask equipped with a stir bar, internal thermometer, 500 mL addition funnel, and distillation apparatus was added MIDA (15.0 g, 102 mmol) and DMSO (50 mL). The solution was heated with an oil bath to an internal temperature of 110-115° C. The borate suspension was transferred to the addition funnel and was continuously agitated with a stream of nitrogen. The borate suspension was added dropwise to the hot MIDA solution over 2 hr 50 min, keeping the internal temperature between 105 and 115° C. After full addition of the borate suspension, the reaction solution was cooled to 60° C. and placed under vacuum (300 mTorr) to distill the reaction to dryness. The resulting foam was cooled to 23° C. and dissolved in 200 mL EtOAc, 50 mL acetone, and 75 mL H$_2$O and poured into 200 mL EtOAc:Acetone (1:1) and 75 mL brine. The mixture was shaken and the aqueous layer was removed and extracted with EtOAc (1×100 mL). The combined organic phases were washed with brine (2×20 mL). The brine wash was back extracted with EtOAc:Acetone (2:1, 1×75 mL) The combined organic phases were dried over MgSO$_4$, filtered, and concentrated in vacuo. The resulting yellow solid was dissolved in 100 mL THF and 1000 mL Et$_2$O was added to precipitate the product. The resulting solid was collected by vacuum filtration to yield propynyl MIDA boronate as a white solid (7.48 g, 77%). TLC (Et$_2$O:Acetone 2:1): R$_f$=0.28, stained by KMnO$_4$. $^1$H-NMR (500 MHz, d$_6$-acetone): δ 4.22 (d, J=17 Hz, 2H), 4.05 (d, J=17 Hz, 2H), 3.18 (s, 3H), 1.83 (s, 3H). $^{13}$C-NMR (125 MHz, d$_6$-acetone): δ 168.6, 62.1, 48.2, 41.1, 4.0. $^{11}$B-NMR (96 MHz, d$_6$-acetone): δ 6.8. HRMS (ESI+): Calculated for C$_8$H$_{11}$BNO$_4$: 196.0781; Found: 196.0784. IR (thin film, cm$^{-1}$): 3009, 2957, 2203, 1790, 1462, 1342, 1290, 1260, 1192, 1169, 1092, 994, 882, 858, 706.

Example 10

Synthesis of Isoprenyl MIDA boronate

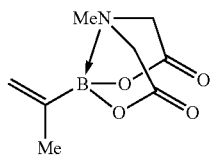

To a 500 mL 3-neck round bottom flask equipped with a stir bar was added B(OMe)$_3$ (12.0 mL, 105 mmol) and THF (100 mL). The solution was cooled to −78° C. Isoprenylmagnesium bromide (0.5 M in THF, 200 mL, 100 mmol) was added dropwise via cannula over 2 hr. The resulting solution was stirred at −78° C. for 1.5 hr, followed by stirring at 23° C. for 2 hr. To a separate 1000 mL 3-neck round bottom flask equipped with a stir bar, internal thermometer, 500 mL addition funnel, and distillation apparatus was added MIDA (29.9 g, 203 mmol) and DMSO (100 mL). The solution was heated with an oil bath to an internal temperature of 110-115° C. The borate suspension was transferred to the addition funnel and was continuously agitated with a stream of nitrogen. The borate suspension was added dropwise to the hot MIDA solution over 2 hr, keeping the internal temperature between 100 and 115° C. After full addition of the borate suspension, the reaction solution was cooled to 60° C. and placed under vacuum (250 mTorr) to distill the reaction to dryness. The resulting foam was cooled to 23° C. and dissolved in 400 mL EtOAc and 150 mL H$_2$O and poured into 400 mL EtOAc:Acetone (1:1) and 150 mL brine. The mixture was shaken and the aqueous layer was removed and extracted with EtOAc (2×200 mL). The combined organic phases were washed with brine (2×20 mL). The brine wash was back extracted with EtOAc:Acetone (2:1, 1×75 mL) The combined organic phases were dried over MgSO$_4$, filtered, and concentrated in vacuo. The resulting white solid was suspended in 150 mL THF and 1500 mL of Et$_2$O was added to precipitate the product. The resulting solid was collected by vacuum filtration to yield isoprenyl MIDA boronate as a white solid (15.91 g, 81%). TLC (Et$_2$O:MeCN 4:1): R$_f$=0.43, stained by KMnO$_4$. $^1$H-NMR (500 MHz, d$_6$-acetone): δ 5.45 (bs, 1H), 5.32 (d, J=2.5 Hz, 1H), 4.21 (d, J=17 Hz, 2H), 4.03 (d, J=17 Hz, 2H), 3.00 (s, 3H), 1.78 (s, 3H). $^{13}$C-NMR (100 MHz, d$_6$-acetone): δ 169.1, 124.4, 62.5, 47.0, 22.0. $^{11}$B-NMR (128 MHz, d$_6$-acetone): 11.2.

Example 11

Large Scale Preparation of 1-Ethynylboronate Ester

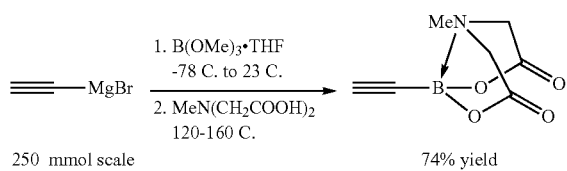

To maximize the yield for this reaction, the MIDA ligand was purified and dried as follows: MIDA was dissolved in a minimum volume of deionized water. Using a mechanical stirrer and a large separatory funnel, the MIDA was precipitated through the dropwise addition of acetone (5× volume relative to water used to dissolve MIDA). The resulting slurry was filtered and the collected white solid was washed with small portions of acetone. This solid was then transferred to a recrystallization dish and placed in a 60° C. oven for 12 h. The resulting solid was ground in a mortar and then placed into a 120° C. oven for four hours. The results are comparable or improved if the MIDA is dried overnight in a vacuum oven.

To an oven-dried 5000-mL 3-neck round-bottomed flask equipped with a magnetic stir bar, a 500-mL pressure-equalizing addition funnel, and two rubber septa was added THF (750 mL) and trimethyl borate (61 mL, 550 mmol, 1.1 equiv) and the resulting solution was cooled to −78° C. The addition funnel was charged with the first portion of ethynyl magnesium bromide solution (500 mL, 250 mmol, 0.50 M in THF) which was then added drop-wise over 35 min. The addition funnel was charged with the second portion of ethynyl magnesium bromide solution (500 mL, 250 mmol, 0.50 M in THF) which was then added drop-wise over 30 min. The reaction vessel was removed from the bath and allowed to warm to ambient temperature over the course of 3 h resulting in a thick white slurry. A separate oven-dried 3000-mL 3-neck round-bottomed flask equipped with a magnetic stir bar, a thermometer, 500 mL addition funnel, and a distillation train was charged with MIDA (162 g, 1100 mmol, 2.2 equiv) and DMSO (750 mL). Using a heating mantle and variac, the suspension was brought to an internal temp of 130° C. To the addition funnel was added 500 mL of hexanes which was then added drop-wise to the MIDA solution (this step was included to azeotropically dry the MIDA solution, head temperature of 60-69° C.) resulting in a homogeneous light-orange solution. The previously prepared suspension of the "ate" complex was added over the course of 1.5 h via cannula transfer under a positive pressure of Ar(g) at a rate such that the internal temperature remained between 120-160° C. After the addition was completed the reaction vessel was washed with THF (2×60 mL) and the washes added via cannula transfer to the reaction vessel containing the MIDA solution. The remaining THF and MeOH were allowed to distill off (~15 min). The reaction vessel was allowed to cool to ambient temperature. The reaction mixture was then transferred to a 6 L separatory funnel. To this was added 1 L of de-ionized water, 1 L of brine, 1.5 L of ethyl acetate, and 1 L of acetone. The organic layer was separated, and the aqueous layer was extracted twice with 500 mL of a 3:2 ethyl acetate: acetone solution and once with 500 mL of ethyl acetate. The combined organic fractions were then washed with 500 mL of brine, and dried with MgSO$_4$. The organic fractions were then concentrated to form a light brown solid. The solid was dissolved in 250 mL of acetone and then was precipitated by the drop-wise addition of 3 L of diethyl ether. The resulting solid was collected via filtration and washed with diethyl ether (2×50 mL). The solid was dissolved using 800 mL of acetone. To this solution was added activated charcoal. This was stirred for 30 min, and then filtered through celite washing with acetone (2×50 mL). The resulting solution was concentrated in vacuo to afford ethynyl MIDA boronate (66.6 g, 74%).

This compound was stable to long-term storage in a vial on the benchtop under air in a subdued light environment (as judged by the $^1$H NMR spectrum acquired after 6 months of storage). TLC (EtOAc) R$_f$=0.46, visualized with KMnO$_4$. $^1$H NMR (400 MHz, CD$_3$CN): δ 4.00 (d, J=17.2 Hz, 2H), 3.87 (d, J=17.2 Hz, 2H), 3.03 (s, 3H), 2.69 (s, 1H). $^{13}$C NMR (100 MHz, CD$_3$CN): δ 168.5, 90.1 (br), 62.2, 48.6. HRMS (ESI): Calculated for C$_7$H$_9$BNO$_4$ (M+H)$^+$: 182.0625; Found: 182.0623.

INCORPORATION BY REFERENCE

All of the U.S. patents and U.S. published patent applications cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. Therefore, the foregoing embodiments are presented by way of example only and, within the scope of the appended claims and equivalents thereto, the invention may be practiced otherwise than as specifically described.

What is claimed is:

1. A method of forming a protected boronic acid, comprising:
reacting in a reaction mixture
an imino-di-carboxylic acid, and
an organoboronate salt represented by formula (I):

[R¹—B(OR²)(OR³)(OR⁴)]⁻M⁺ (I);

wherein
R¹ is an organic group,
R², R³ and R⁴ independently are selected from the group consisting of an alkyl group and an aryl group, and
M⁺ is selected from the group consisting of a metal ion, a metal halide ion and an ammonium ion; and
the reaction mixture further comprises a polar aprotic solvent;
wherein the reacting comprises maintaining the reaction mixture at a temperature of at least 100° C.; and
thereby forming a protected organoboronic acid represented by formula (III) in the reaction mixture:

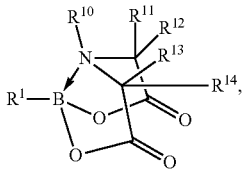

(III)

wherein R¹⁰, R¹¹, R¹², R¹³ and R¹⁴ independently are selected from the group consisting of a hydrogen group and an organic group.

2. The method of claim 1, wherein R¹ is an alkyl group, a heteroalkyl group, an alkenyl group, a heteroalkenyl group, an alkynyl group, a heteroalkynyl group, an aryl group, a heteroaryl group, or a combination of at least two of these groups.

3. The method of claim 1, wherein R¹ is represented by formula (IV):

Y—R⁵—(R⁶)ₘ— (IV), wherein
Y is a halogen group or a pseudohalogen group;
R⁵ is an aryl group or a heteroaryl group;
R⁶ is an alkyl group, a heteroalkyl group, an alkenyl group, a heteroalkenyl group, an alkynyl group, a heteroalkynyl group, an aryl group, a heteroaryl group, or a combination of at least two of these groups; and
m is 0 or 1.

4. The method of claim 3, wherein R⁵ is a heteroaryl group.

5. The method of claim 1, wherein R¹ is a heterocyclic group, an alkynyl group or an alkenyl group.

6. The method of claim 5, wherein said heterocyclic group is selected from the group consisting of pyridine, indole, isoindole, indazole, purine, indolizidine, quinoline, isoquinoline, quinazoline, pteridine, quinolizidine, pyrrole, pyrazine, pyridazine, pyrimidine, imidazole, pyrasole, isoxazole, oxazole, thiazole, benzthiazole, furan, benzofuran, thiophene and benzothiophene.

7. The method of claim 1, wherein R¹ is a 2-heterocyclic group selected from the group consisting of 2-pyridyl, 2-indolyl, 2-isoindolyl, 2-indazolyl, 2-purinyl, 2-indolizidinyl, 2-quinolinyl, 2-isoquinolinyl, 2-quinazolinyl, 2-pteridinyl, 2-quinolizidinyl, 2-pyrrolyl, 2-pyrazinyl, 2-pyridazinyl, 2-pyrimidinyl, 2-imidazolyl, 2-pyrasolyl, 2-isoxazolyl, 2-oxazolyl, 2-thiazolyl, 2-benzthiazolyl, 2-furyl, 2-benzofuryl, 2-thiophenyl, and 2-benzthiophenyl.

8. The method of claim 1, wherein R², R³ and R⁴ are each independently an alkyl group containing from 1 to 4 carbon atoms.

9. The method of claim 8, wherein said alkyl group is methyl (—CH₃) or isopropyl (—CH(CH₃)₂).

10. The method of claim 1, wherein M⁺ is selected from the group consisting of Li⁺, Na⁺, K⁺, MgX⁺, CaX⁺, Zn⁺, Bu₄N⁺, and Me₄N⁺; and X is F, Cl, Br or I.

11. The method of claim 10, wherein M⁺ is Li⁺ or MgX⁺.

12. The method of claim 1, wherein R¹⁰ is methyl, and each of R¹¹, R¹², R¹³ and R¹⁴ is hydrogen.

13. The method of claim 1, wherein the polar aprotic solvent is selected from the group consisting of tetrahydrofuran (THF), dioxane, dimethyl formamide (DMF), dimethyl sulfoxide (DMSO), toluene and xylene.

14. The method of claim 1, wherein the polar aprotic solvent is DMSO.

15. The method of claim 1, wherein the reaction mixture is at a temperature of from 100° C. to 200° C.

16. The method of claim 1, further comprising:
reacting in a reaction mixture
an organohalide or an organo-pseudohalide (V), an organolithium reagent, and a boronate ester, to form the organoboronate salt (VI), as represented by the following reaction scheme:

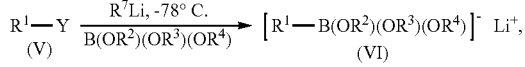

wherein Y is a halogen or a pseudohalogen; and R⁷ is a hydrocarbon group.

17. The method of claim 1, further comprising:
reacting in a reaction mixture
an organic compound (VII), and
a first organolithium reagent to form a second organolithium reagent (VIII); and
reacting in a reaction mixture said second organolithium reagent (VIII), and
a boronate ester to form a organoboronate salt (VI), as represented by the following reaction scheme:

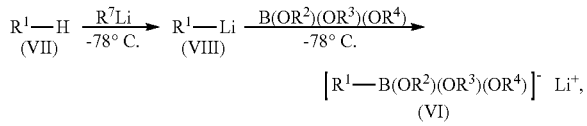

wherein R⁷ is a hydrocarbon group.

18. The method of claim 1, further comprising:
reacting in a reaction mixture an organic compound (VII), and MgCl/LiCl 2,2,6,6-tetramethylpiperidyl amide to form a Grignard reagent (IX); and
reacting in a reaction mixture said Grignard reagent (IX) and a boronate ester to form a organoboronate salt (X), as represented by the following reaction scheme:
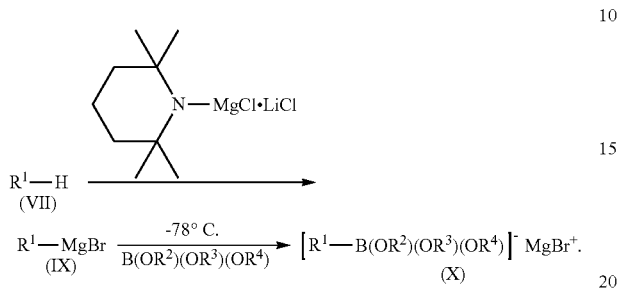
* * * * *